(12) United States Patent
Karp et al.

(10) Patent No.: US 10,973,846 B2
(45) Date of Patent: Apr. 13, 2021

(54) WATER-ACTIVATED MUCOADHESIVE COMPOSITIONS TO REDUCE INTESTINAL ABSORPTION OF NUTRIENTS

(71) Applicant: The Brigham and Women's Hospital, Inc., Boston, MA (US)

(72) Inventors: Jeffrey M. Karp, Brookline, MA (US); Yuhan Lee, Cambridge, MA (US); Ali Tavakkoli, Boston, MA (US); Tarawatie E. Deelman, Boston, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 112 days.

(21) Appl. No.: 15/763,018

(22) PCT Filed: Sep. 26, 2016

(86) PCT No.: PCT/US2016/053781
§ 371 (c)(1),
(2) Date: Mar. 23, 2018

(87) PCT Pub. No.: WO2017/053970
PCT Pub. Date: Mar. 30, 2017

(65) Prior Publication Data
US 2020/0046754 A1 Feb. 13, 2020

Related U.S. Application Data

(60) Provisional application No. 62/232,283, filed on Sep. 24, 2015.

(51) Int. Cl.
*A61K 31/737* (2006.01)
*A61P 3/10* (2006.01)
*A61K 47/38* (2006.01)
*A61K 9/00* (2006.01)
*A61K 9/107* (2006.01)

(52) U.S. Cl.
CPC ............ *A61K 31/737* (2013.01); *A61K 47/38* (2013.01); *A61P 3/10* (2018.01); *A61K 9/0053* (2013.01); *A61K 9/107* (2013.01)

(58) Field of Classification Search
CPC ......... C08B 5/14; C08B 31/063; C08B 33/02; C08B 37/0021; C08B 37/0069; C08B 37/0075
See application file for complete search history.

(56) References Cited

U.S. PATENT DOCUMENTS

| | | | |
|---|---|---|---|
| 3,432,489 A * | 3/1969 | Hirota | C07H 23/00 536/118 |
| 4,522,811 A | 6/1985 | Eppstein et al. | |
| 4,866,856 A | 9/1989 | Feeley | |
| 4,885,281 A | 12/1989 | Hanstein et al. | |
| 5,013,557 A | 5/1991 | Tai | |
| 5,246,697 A | 9/1993 | Conte et al. | |
| 5,294,434 A | 3/1994 | King et al. | |
| 5,321,013 A | 6/1994 | Zagnoli et al. | |
| 5,464,828 A | 11/1995 | Katayama et al. | |
| 5,563,258 A | 10/1996 | Ochi et al. | |
| 5,595,977 A * | 1/1997 | Dyrsting | A61K 38/14 514/35 |
| 5,661,137 A | 8/1997 | Zagnoli | |
| 5,718,923 A | 2/1998 | Matsuda et al. | |
| 5,968,906 A | 10/1999 | Kashimura et al. | |
| 6,391,294 B1 * | 5/2002 | Dettmar | A61K 9/0014 424/78.11 |
| 6,391,860 B1 | 5/2002 | McGrath | |
| 6,555,137 B1 | 4/2003 | Yamazaki et al. | |
| 6,773,722 B2 | 8/2004 | Zagnoli et al. | |
| 10,716,802 B2 | 7/2020 | Karp et al. | |
| 2007/0190139 A1 | 8/2007 | Zerbe et al. | |
| 2008/0319230 A1 | 12/2008 | Sigl et al. | |
| 2009/0196896 A1 | 8/2009 | Patton et al. | |
| 2010/0172967 A1 | 7/2010 | Nemoto et al. | |
| 2011/0021455 A1 | 1/2011 | Chesnoy et al. | |
| 2011/0229556 A1 | 9/2011 | Irvine et al. | |
| 2012/0039981 A1 | 2/2012 | Pedersen et al. | |
| 2012/0064139 A1 | 3/2012 | McGrath et al. | |
| 2013/0274209 A1 | 10/2013 | Colombo | |
| 2020/0289546 A1 | 9/2020 | Karp et al. | |

FOREIGN PATENT DOCUMENTS

| | | |
|---|---|---|
| CA | 2067070 | 10/1992 |
| EP | 0511703 | 11/1992 |
| EP | 0245855 | 1/1993 |
| EP | 0437406 | 3/1993 |

(Continued)

OTHER PUBLICATIONS

Maggi et al., AAPS PharmSciTech, 2000; 1(3), article 26, 8 pages. (Year: 2000).*
EP Office Action in European Appln. No. 16849871, dated Jun. 24, 2020, 8 pages.
'en.wikipedia.org' [online]. "Freeze-drying," dated Sep. 18, 2015 [retrieved on Nov. 22, 2016], Retrieved from the Internet <URL: https://en.wikipedia.org/w/index.php?title=Freezedrying&oldid=681682674> 7 pages.
'en.wikipedia.org' [online]. "Coacervate," dated May 20, 2015 [retrieved on Nov. 22, 2016]. Retrieved from the Internet <URL: https://en.wikipedia.org/w/index.php?title=Coacervate&oldid=663181907> 2 pages.

(Continued)

*Primary Examiner* — Jonathan S Lau
(74) *Attorney, Agent, or Firm* — Fish & Richardson P.C.

(57) ABSTRACT

This disclosure relates to compositions including formulated sucralfate or other aluminum-crosslinked sulfated agents for delivery of agents to biological surfaces and/or the modulation of nutrient absorption through the intestinal lining as well as methods for the manufacture of and the use of these compositions for treating disorders including diabetes type II and clinical obesity that require a modulation of certain nutrients to the body.

16 Claims, 20 Drawing Sheets

(56) References Cited

FOREIGN PATENT DOCUMENTS

| EP | 2482822 | 8/2012 |
|---|---|---|
| RU | 2422133 | 6/2011 |
| WO | WO 1989/005645 | 6/1989 |
| WO | WO 2011/041509 | 4/2011 |
| WO | WO 2014/151565 | 9/2014 |

OTHER PUBLICATIONS

'en.wikipedia.org' [online]. "List of water-miscible solvents," dated Mar. 31, 2015[retrieved on Nov. 22, 2016]. Retrieved from the Internet <URL: https://en.wikipedia.org/w/index.php?title=list_ofwater-miscible_solvents&oldid=654319850> 3 pages.

'en.wikipedia.org' [online]. "Propylene glycol," dated Sep. 19, 2015 [retrieved on Nov. 22, 2016]. Retrieved from the Internet <URL: https://en.wik1pedia.org/w/index.php?title=Propylene_glycol&oldid=681710532> 7 pages.

'www.chemicaprocessing.com' [online]. "Marion Mixers: Comparing Microwave to Conventional Heating and Drying Systems," dated Jun. 12, 2015 [retrieved on Nov. 22, 2016]. Retrieved from the Internet <URL: http://www.chemicalprocessing.com/assets/wp_downloads/pdf/comparing-microwave-tocovnetional-heating-drying-systems-v2.pdf > 7 pages.

'www.puecchner.com' [online]. "Microwave Vacuum Drying for advanced Process Technology," Oct. 29, 2012 [retrieved on Nov. 22, 2016). Retrieved from the Internet <URL: http://www.pueschner.com/downloads/vacuumdrying.pdf> 8 pages.

Beheshti et al., "Comparison of topical sucralfate and silver sulfadiazine cream in second degree burns in rats," Adv Clin Exp Med, 2013, 22: 481-487.

Couzin, "Bypassing Medicine to Treat Diabetes," Science, 2008, 320: 438-440.

Cummings and Flum, "Gastrointestinal Surgery as a Treatment for Diabetes," J. Am. Med. Assoc., 2008, 299: 341-343.

Gersin et al., "Open-label, sham-controlled trial of an endoscopic duodenojejunal bypass liner for preoperative weight loss in bariatric surgery candidates," Gastrointest. Endosc. 2010, 71: 976-82.

Gupta et al., "Topical Sucralfate Treatment of Anal Fistulotomy Wounds: A Randomized Placebo-Controlled Trial," Diseases of the Colon & Rectum, 2011, 54: 699-704.

Higo et al., "A Novel Evaluation Method of Gastric Mucoadhesive Property in Vitro and the Mucoadhesive Mechanism of Tetracycline-Sucralfate Acidic Complex for Eradication of Helicobacter pylori," Pharm. Res, 2004, 21: 413-419.

International Preliminary Report on Patentability in International Application No. PCT/US2016/053781, dated Apr. 5, 2018, 8 pages.

International Preliminary Report on Patentability in International Application No. PCT/US2014/26007, dated Sep. 15, 2015, 9 pages.

International Search Report and Written Opinion in International Application No. PCT/US2016/053781, dated Jan. 26, 2017, 15 pages.

International Search Report and Written Opinion in International Application No. PCT/US2014/26007, dated Jul. 7, 2014, 16 pages.

Malbert et al., "Duodenal Bulb Control of the Flow Rate of Digesta in the Fasted and Fed Dog," J. Physiol., 1989, 409:371-384.

Markham et al., "Topical sucralfate for erosive irritant diaper dermatitis," Archives of Dermatology, 2000, 136: 1199-200.

New et al., "Assessing the prevalence, monitoring and management of chronic kidney disease in patients with diabetes compared with those without diabetes in general practice," Diabetic Medicine, 2007, 24: 364-369.

Ochi, "Chemistry of Sucralfate" in Sucralfate: From Basic Science to the Bedside, Chapter 5, 1995, pp. 53 and 55.

Office Action in U.S. Appl. No. 14/776,594, dated Jan. 18, 2017, 12 pages.

Office Action in U.S. Appl. No. 14/776,594, dated Nov. 28, 2017, 12 pages.

Pories et al., "Who Would Have Thought It? An Operation Proves to Be the Most Effective Therapy for Adult-Onset Diabetes Mellitus," Ann. Surg., 1995, 222: 339-350.

Ritz et al., "Nephropathy in patients with type 2 diabetes mellitus," New Engl. J. Med., 1999, 341: 1127-1133.

Rubino et al., "Potential of Surgery for Curing Type 2 Diabetes Mellitus," Ann. Surg., 2002, 236: 554-559.

Schouten et al., "A multi-center, randomized efficacy study of th EndoBarrier™ Gastrointestinal Liner for pre-surgical weight loss prior to bariatric surgery," Ann. Surg., 2010, 251(2), 236-243.

Slomiany et al., "Enhancement of the protective qualities of gastric mucus by sucralfate: Role of phosphoinositides," Am. J. of Med., 1991, 91: 30S-36S.

Tasman-Jones et al., "Sucralfate interactions with gastric mucus," Am. J. Med., 1989, 86: 5-9.

Zuidam and Shimoni, "Overview of Microencapsulates for Use in Food Products or Processes and Methods to Make Them" in Encapsulation Technologies for Active Food Ingredients and Food Processing, Chapter 2, 2010, p. 15.

Office Action in U.S. Appl. No. 14/776,594, dated May 8, 2019, 13 pages.

Extended European Search Report in Application No. 16849871.5, receipt date May 6, 2019, 10 pages.

* cited by examiner

AF-LuCI particles that can be orally delivered and instantly form a barrier coating on stomach and intestine Dry particles in a pill or a capsule Dry particles in a pill or a capsule that can instantly form a barrier coating on stomach and intestine with no potential side effects No Side Effects Coating on stomach and/or intestine Particles dispersed in stomach and/or intestine

FIG. 1

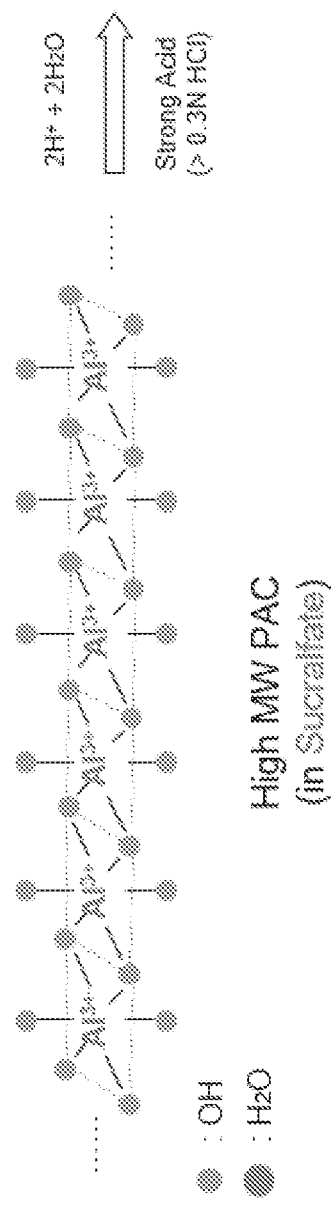
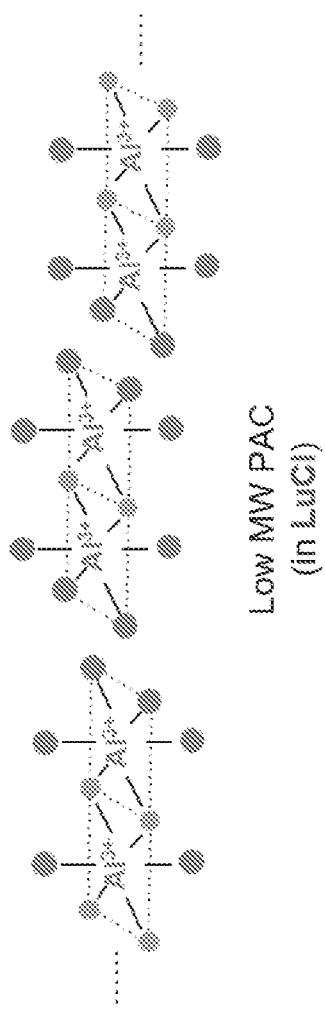
FIG. 4A
FIG. 4B

Thermogravimetric analysis (TGA) thermal curves (a-b) of sucralfate and AF-LuCl, and their first derivative curves (c-d)

Barrier to Glucose: AF-LuCls show excellent barrier function to glucose in vivo (rats)

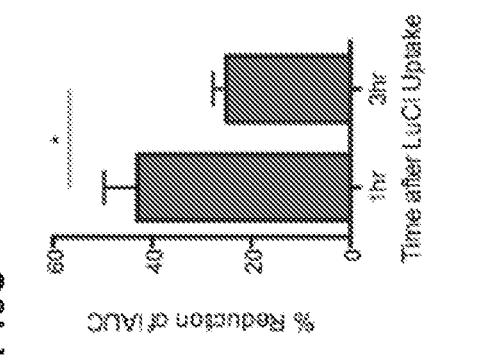
FIG. 19A    FIG. 19B
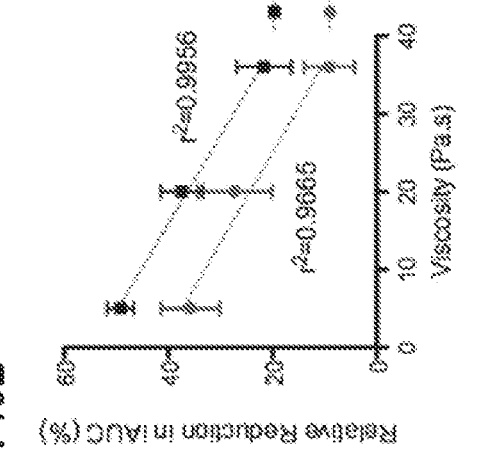
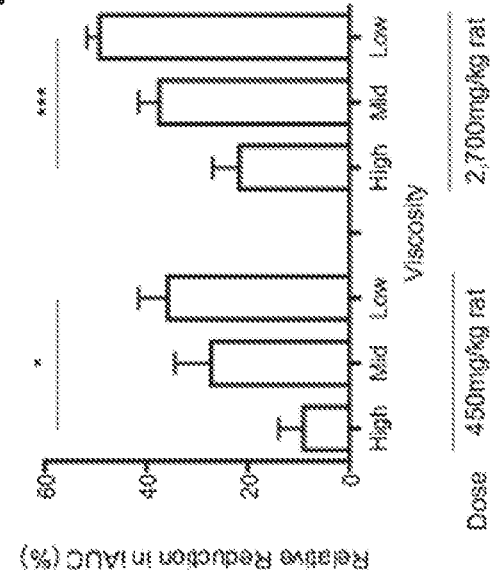
FIG. 19C

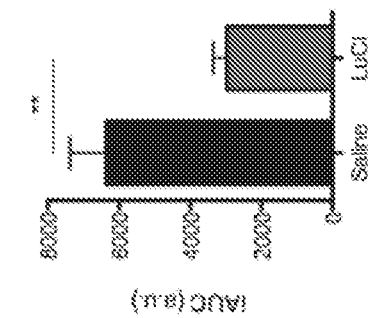
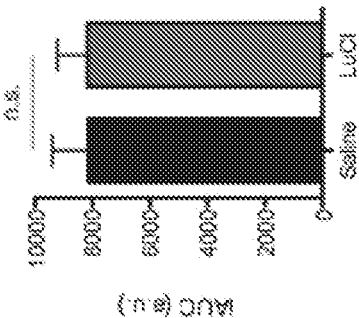
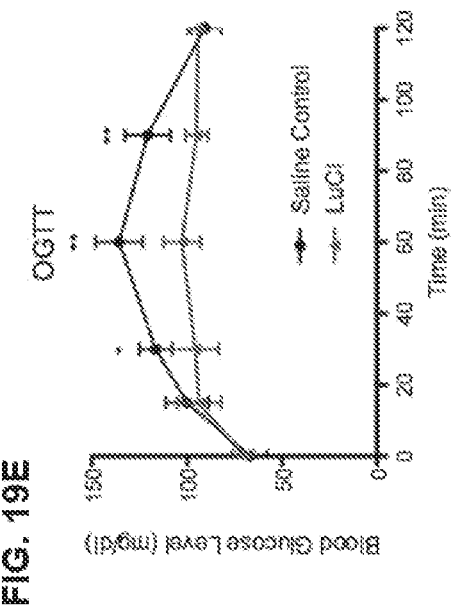
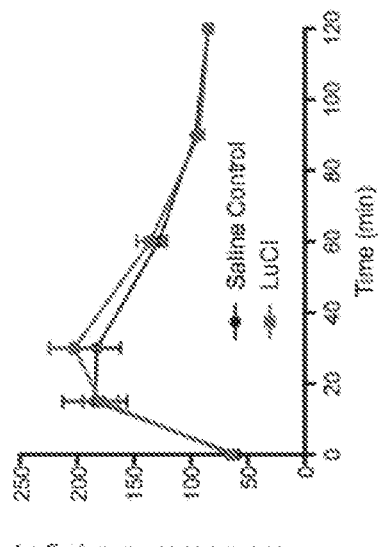
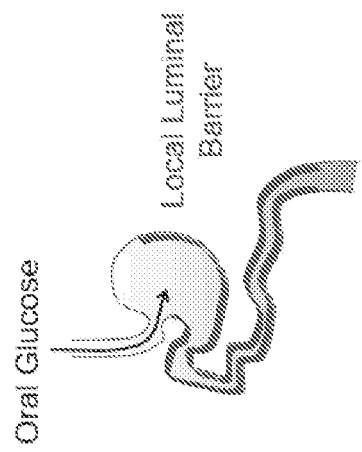
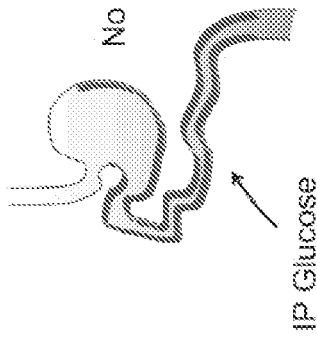

WATER-ACTIVATED MUCOADHESIVE COMPOSITIONS TO REDUCE INTESTINAL ABSORPTION OF NUTRIENTS

CLAIM OF PRIORITY

This application is a 371 U.S. National Phase Application of PCT Application No. PCT/US2016/053781, filed on Sep. 26, 2016, which claims the benefit of U.S. Provisional Application Ser. No. 62/232,283, filed on Sep. 24, 2015. The entire contents of the foregoing are incorporated herein by reference.

FIELD OF THE INVENTION

The field of this disclosure relates to compositions that can be topically delivered to easily form coatings on biological surfaces and can be used for the delivery of agents and/or for barrier properties.

BACKGROUND

Type-2 diabetes mellitus (T2DM) affects about 11.3% of the U.S. adult population with 35% of the U.S. adults having pre-diabetic symptoms. U.S. healthcare costs due to diabetes exceed $174 billion annually. The incidence of T2DM continues to increase in parallel with the obesity epidemic, and the present treatment algorithm for T2DM consists of a regimen of medication that is suboptimal for many patients. Current strategies for T2DM management and treatment range from commercial diets and drugs to surgical approaches. Although each of these strategies may have merit, considerable limitations exist. While diets carry limited risk, they are often unsuccessful. Drugs that lower blood glucose level (e.g., metformin) are also available, but the use and success of these drugs are limited due to side effects, poor compliance, and low efficacy. Patients also have options of bariatric surgeries, which include laparoscopic adjustable gastric banding (LAGB), bilio-pancreatic diversion (BPD), laparoscopic sleeve gastrectomy (LSG), and Roux-en-Y bypass (RYGB) (W. J. Pories et al., Ann. Surg., 222, 339-350 (1995); F. Rubino et al., Ann. Surg., 236, 554-559, (2002); J. Couzin, Science, 320, 438-440 (2008); D. E. Cummings and D. R. Flum, J. Am. Med. Assoc. 299, 341-343 (2008)).

Originally developed for weight loss, RYGB and similar surgeries have been recognized as the gold standard bariatric operation to treat obesity-related T2DM. Multiple reports have confirmed that obese T2DM patients who undergo RYGB surgery immediately experience significant improvement or complete resolution of their T2DM prior to any significant weight loss. Accordingly, many have classified RYGB as a "metabolic" operation and a "cure" for T2DM. However, due to potential surgical complications (e.g., leaks at the surgical site and infections) over 70% of patients, although overweight or mildly obese, do not meet the NIH criteria for weight loss surgery and struggle with suboptimal medical treatments (American Diabetes Association. V. Diabetes Care. Diabetes Care, 35 (2012)).

This result highlights the need for less invasive alternatives that replicate the metabolic success of RYGB and other bariatric surgeries that can be offered to a wider patient population. The success of RYGB in remitting T2DM has inspired significant research into mechanisms underlying this observation with significant interest in the role of duodenal isolation. As a less invasive implantable alternative to RYGB, a duodeno-jejunal bypass sleeve (DJBS) was developed to prevent contact between food and duodenal mucosa, and has shown promising results in remitting T2DM. However, the sleeve implant requires placements using endoscopy and is associated with a high rate of bleeding or obstruction. In addition, this technique requires annual device removal (R. Schouten et al., Ann. Surg., 251(2), 236-243 (2010); K. S. Gersin et al., Gastrointest. Endosc. (2010)). Therefore, there is a clear and urgent need for a less invasive T2DM treatment option that is easy to administer and does not present risks associated with surgical procedures.

SUMMARY

The present disclosure describes water-activated mucoadhesive hydratable compositions (also referred to herein as Acid-Free Luminal Coating of the Intestine particles, abbreviated as "AF-LuCI" particles) that can be utilized to temporarily coat biological surfaces such as the mucosa of the gastrointestinal tract (e.g., oral mucosa, the stomach, duodenum, the small intestines, and colon) to thereby deliver agents to mucosal surface of the bowel, provide a protective coating of the intestine, and/or reduce absorption of nutrients, such as glucose, through the intestinal lining into the bloodstream. Various medical conditions (e.g., obesity, type II diabetes (T2DM), and pre-diabetes can be treated or can benefit from a reduction in the absorption of nutrients (e.g., glucose) that can be achieved by generating a barrier that decreases absorption of the nutrients by the tissue. Thus, the present disclosure also describes therapeutic methods using such compositions to treat disorders such as obesity and diabetes.

In one aspect, the disclosure relates to a water-based, liquid hydratable compositions. The compositions include one or more aluminum cross-linked sulfated agents that can form a paste following contact with an aqueous liquid in the absence of acid. In another aspect, the disclosure relates to hydratable compositions, e.g., in a dry form, that include particles each including one or more aluminum cross-linked sulfated agents that can form a paste following contact with an aqueous liquid in the absence of acid. In some embodiments, the compositions include a complex coacervate having a complex of two or more oppositely charged agents where one agent is a sulfated agent.

These compositions can have the following chemical structure:

$$C_{12}H_{30}Al_8S_8 \cdot (x-n)Al(OH)_3 \cdot [Al-(OH)_i]_m \cdot zH_2O$$

wherein x is less than or equal to 8;

$0 < n < x$;

m is greater than or equal to 2;
i=1, 2, or 3; and $z < 3(x-n) + (6-i)m$.

The sulfated agents in these hydratable compositions can comprise any one or more of, consist essentially of, or can be selected from the group consisting of sucralfate, sulfated dextran, sulfated dextrin, sulfated amylopectin, sulfated amylose, sulfated cellulose, carrageenan, chondroitin sulfate, glucose sulfate, sucrose sulfate, heparin, heparin sulfate, and raffinose sulfate.

The hydratable compositions can include a non-aqueous liquid carrier and when rehydrated, the viscous liquid composition can have a viscosity in the range of 1 to 1000 Pascal-seconds (Pa·s), regardless of the pH of the liquid. The hydratable compositions can be dissolved in an amount of liquid sufficient to obtain a viscous liquid composition having a viscosity in the range of 10 to 100 Pa·s, e.g., 25 to 75 Pa·s. In various embodiments, the particles can range in size from about 0.1 to about 500 microns.

The hydratable compositions can be rehydrated by the addition of an aqueous solvent, and following hydration the particles in the composition stably adhere to a mucin coated surface under shear stress conditions. In various examples, when hydrated, the compositions form a barrier that when prepared at 10 mg/ml and applied to 1 cm$^2$ surface area cellulose nitrate filter with 0.45 micron holes in a Franz diffusion chamber exhibits less than 60% permeation of glucose 5 minutes after addition of 120 g/L glucose solution to the top chamber, and more preferably less than 40% permeation.

The hydratable compositions can release less than about 2.0 weight/weight percent of their original aluminum content in the presence of an aqueous liquid. In some embodiments, the hydratable compositions release <0.5% aluminum by weight in the presence of an aqueous liquid and when administered to a subject form an effective nutrient barrier in the gastrointestinal tract. The nutrient barrier properties (e.g. to glucose) do not appreciably change when the compositions are dried and rehydrated in the intestinal tract.

In some embodiments, the hydratable compositions also comprise one or more antimicrobial agents, e.g., iodine, silver ions, and chlorine, or can include a biologically active substance such as a biomolecule, e.g., any one or more of enzymes, receptors, neurotransmitters, hormones, cytokines, cell response modifiers such as growth factors and chemotactic factors, antibodies, vaccines, haptens, toxins, bacteria, small molecules, neutraceuticals, interferons, ribozymes, antisense agents, plasmids, DNA, and RNA. In some embodiments, the hydratable compositions (or the particles in the hydratable compositions) are cross-linked to the agents and/or the biologically active substance. In some embodiments, the hydratable compositions are loaded with the agents and/or the biologically active substance. In some embodiments, the agents and/or the biologically active substance are encapsulated in the hydratable composition (or in the particles of the hydratable compositions).

In various implementations, the hydratable compositions can be hydrated into a sticky paste and the paste can be dehydrated again to form the hydratable compositions.

In another aspect, the disclosure includes methods of making a stable, sulfated agent hydratable compositions. The methods include mixing a sulfated agent with an acid solution (e.g., 0.1-1.0 N HCl solution) to form a viscous ("sticky paste") precipitate; dehydrating, e.g., rapidly dehydrating, the precipitate by mixing (e.g., by vortexing, homogenization, or sonication) the viscous precipitate with a sufficient amount, e.g., at least 30 v/v %, of a water-miscible solvent for a time sufficient to obtain a particle suspension; and removing particles from the suspension (e.g., removing the solvent) to obtain a stable, sulfated agent hydratable composition.

These methods can further include further drying the stable, sulfated agent hydratable composition to remove any remaining solvent.

In some embodiments, the methods include the steps of mixing a sulfated agent with an acid solution to form a precipitate; adding water-miscible common solvents to the precipitate; stirring to form a suspension in brittle particle form; and drying in vacuum to evaporate solvents. In some embodiments, the water-miscible common solvent is ethanol, methanol, dimethylsulfoxide (DMSO), or acetone.

In various embodiments, the water-soluble solvent or water-miscible solvent can include any one or more of an alcohol (e.g., methanol, ethanol, isopropanol, n-propanol, reagent alcohol, 2-butoxiethanol, and furfuryl alcohol), acetone, dimethyl sulfide (DMSO), N,N-dimethyl formamide (DMF), acetonitrile, 1,4-dioxane, tetrahydrofuran (THF), acetic acid, acetaldehyde, 1,2-butandiol, 1,3-butandiol, 1,4-butandiol, butyric acid, diethanolamine, diethylenetriamine, dimethoxyethane, ethylamine, ethylene glycol, formic acid, glycerol, methyl diethanolamine, methyl isocyanide, 1,3-propanediol, 1,5-pentanediol, propanoic acid, propylene glycol, pyridine, and triethylene glycol.

In another embodiment, the disclosure includes other methods of making a stable, sulfated agent hydratable composition, by mixing a sulfated agent with an acid solution (e.g., 0.1-1.0 N HCl solution) to form a viscous ("sticky paste") precipitate; and rapidly dehydrating the precipitate by applying microwave energy for a time sufficient to obtain dried particles. Any of these methods can further include grinding or crushing the dried hydratable composition to form a powder.

In another aspect, the disclosure includes methods of modulating nutritional absorption in a subject having a disorder in need of such treatment. The methods include selecting a subject suffering from a disorder requiring modulation of nutritional absorption; and administering to the subject a therapeutically effective amount of any of the hydratable compositions described herein. For example, the administering can be done by direct application of the composition, e.g., via endoscopy, needle, brush, or spray, or wherein the composition is in the form of a pill, tablet, capsule, or gel-cap. In these methods, the disorder can be, for example, type II diabetes or obesity.

In these methods the composition can be encapsulated in a degradable capsule, e.g., a capsule is configured to degrade in a specific region of the GI tract. For example, the capsule can include a pH-sensitive material, e.g., one that degrades in alkaline or in acidic conditions. The methods can include the use of compositions that are altered to allow specific cranio-caudal distribution of the composition. For example, the composition can have a change in pH sensitiveness, or a change in size of the composition, or a change in the electrostatic charge of the composition. In some embodiments, it coats a specific length of the bowel.

In another aspect, the disclosure includes dehydrated acid-pretreated compositions that include particles comprising aluminum cross-linked sulfated agents that can form a paste following contact with water in the absence of acid and dry aluminum cross-linked sulfated compositions for use as an aqueous film forming barrier with aluminum content less than 15.5% that forms a viscous paste in the presence of water. These compositions, when in the presence of gastrointestinal fluid, can in certain embodiments, release less than 2% wt/wt aluminum.

In another aspect, any and all of the hydratable compositions described herein can be used for treating disorders of the gastrointestinal tract and/or nutritional disorders and/or obesity, and/or T2D including its associated comorbidities, or for providing a temporary coating of a portion of the gastrointestinal tract. In some embodiments, the portion of gastrointestinal tract is the proximal gastrointestinal tract.

In some embodiments, the hydratable compositions provided herein form a paste upon hydration (e.g., re-hydration), such as hydration or rehydration in an aqueous fluid, regardless of the pH of that fluid, that has a viscosity that is, e.g., greater than 35 Pa·s (e.g., greater than 40, 45, 50, 55, or 60 Pa·s). Some embodiments further include placing the hydratable composition into a coating material (e.g., gelatin or hydroxypropyl methylcellulose (HPMC), or any combination of the coating materials described herein or known in the art) to form a coating around the hydratable composition in the particular composition. Some embodiments further include adding the hydratable compositions to a food substance or food additive.

Also provided are methods of reducing nutritional absorption in a subject in need of such treatment (e.g., a subject having a disorder in need of such treatment, e.g., such as type II diabetes (T2DM), obesity, or pre-diabetes). These methods include, consist of, or consist essentially of selecting a subject in need of such treatment (e.g., a subject suffering from a disorder requiring modulation (e.g., decrease) of nutritional adsorption (e.g., obesity, pre-diabetes, or type II diabetes (T2DM)) or a subject in need of weight loss) and administering to the subject a therapeutically effective amount of any of the hydratable compositions provided herein, e.g., in the form of a tablet, capsule, or pill.

The disclosure also provides methods of decreasing the risk of developing type II diabetes (T2DM) in a subject having pre-diabetes (e.g., as compared to another subject having pre-diabetes that does not receive treatment or receives a different treatment) that include, consist of, or consist essentially of selecting a subject having pre-diabetes and administering to the selected subject a therapeutically effective amount of any of the hydratable compositions provided herein.

Also provided are methods of promoting weight loss in a subject that include, consist of, or consist essentially of selecting a subject and administering to the selected subject a therapeutically effective amount of any of the hydratable compositions provided herein. In some embodiments, the subject is obese, has type II diabetes (T2DM), or is pre-diabetic. In some embodiments, the subject has a BMI of greater than 30, a BMI between about 25 and about 30, a BMI of between about 20 and 25, or a BMI of between about 18.5 and 25.

The disclosure also provides methods of treating an oral, gastric, stomach, or intestinal ulcer or wound in a subject (e.g., a subject having mucositis, cancer sore(s), ulcerative colitis, or Crohn's disease) that include, consist of, or consist essentially of selecting a subject having an ulcer or wound and administering to the selected subject a therapeutically effective amount of any of the hydratable compositions provided herein.

Also provided are methods of treating a microbial infection or colonization in a subject in need of such treatment (e.g., a subject having a disorder in need of such treatment) that include, consist of, or consist essentially of selecting a subject in need of such treatment (e.g., a subject having a disorder requiring treatment of a microbial colonization or infection) and administering to the subject a therapeutically effective amount of any of the hydratable compositions described herein. For these uses, the compositions provide a protective effect.

In some embodiments of any of these methods, the hydratable compositions are encapsulated or delivered in a degradable capsule. In some embodiments, the capsule is configured or designed to degrade in a specific portion of the GI tract. In some embodiments, the capsule includes, consists of, or consists essentially of a pH-sensitive material (e.g., a pH-sensitive material that degrades in alkaline conditions). In some embodiments, the composition is altered or selected to allow specific cranio-caudal distribution of the composition. For example, the alteration of the composition is a change in the pH sensitiveness of the composition, a change in the electrostatic charge of the composition, and/or a change in the size of the composition.

In some embodiments, the hydratable compositions contain, are cross-linked to, are attached to (e.g., physically attached), or combined with an antimicrobial agent (e.g., any of the exemplary antimicrobial agents described herein or known in the art). For example, the antimicrobial agent can be selected from the group of iodine, silver ions, and chlorine, or selected from the group of iodine, silver ions, bismuth (e.g., bismuth salicylate), and chlorine.

Also provided are hydratable compositions as described herein for use in reducing nutritional absorption in a subject in need of such treatment (e.g., a subject having a disorder in need of such treatment, e.g., such as type II diabetes (T2DM), obesity, or pre-diabetes), decreasing the risk of developing type II diabetes (T2DM) in a subject having pre-diabetes, promoting weight loss in a subject, or treating a microbial infection or colonization in a subject in need thereof.

In some embodiments, the hydratable compositions described herein are used in combination with or as a supplement to an additional agent, e.g., a therapeutic agent, to treat disorders such as diabetes, obesity, pre-diabetes, and mucositis. For example, the additional agent can be a therapeutic agent that is known to be useful to treat the disorder. The additional agent also can be an agent that imparts a beneficial attribute to the therapeutic composition (e.g., an agent that affects the viscosity of the composition).

The combination therapies contemplated herein include, for example, administration of one or more hydratable compositions as described herein and one or more additional agent(s) in a single pharmaceutical formulation, as well as administration of one or more compositions as described herein and one or more additional agent(s) in separate pharmaceutical formulations. For example, the additional agents can be administered simultaneously or sequentially over a period of time.

For example, in various embodiments, the hydratable compositions described herein are administered with (e.g., simultaneously or sequentially) one or more of the following diabetes therapeutic agents: insulin, a metformin, sulfonylurea, alpha-glucosidase inhibitor, thiazolidinediones, amylin analog, bile acid sequestrant, DPP-4 inhibitors, dopamine agonist, incretin mimetics, non-sulfonylurea secretagogues, and meglinitides (Repaglinide/Prandin, Nateglinide/Starlix®). In other embodiments, the hydratable compositions are administered with one or more of the following obesity therapeutic agents: orlistat, lorcaserin, sibutramine, rimonabant, metformin, exenatide, pramlintide (Symlin®), and topiramate/phentermine (Qsymia®).

The agents and compositions set forth herein are for illustrative purposes and not intended to be limiting. The combinations can also include more than one additional agent, e.g., two or three additional agents if the combination is such that the resulting composition can perform its intended function.

The new methods also include the use of the hydratable compositions described herein together with one or more surgical procedures, e.g., to reduce weight. For example, in one embodiment, the compositions are administered prior to or following a weight loss surgery including: RYGB, LAGB, BPD, and gastrectomy (e.g., sleeve gastrectomy). In some instances, the hydratable compositions are administered in addition to lifestyle changes. The nutrient absorption-reducing hydratable compositions are administered with a limited calorie intake diet and exercise. To practice the methods described herein, the hydratable compositions having one or more components described herein can be administered orally.

The new hydratable compositions can be designed to form a temporary protective layer in any portion of the gastrointestinal (GI) tract, regardless of the pH of the fluid in that portion of the GI tract. Thus, the new compositions can be used to temporarily coat the lining of portions of the GI tract (e.g., the stomach, duodenum, and the small intestines) to thereby reduce absorption of nutrients, such as glucose, through the intestinal lining into the bloodstream. As a result, various medical conditions (e.g., obesity, type II diabetes (T2DM), and pre-diabetes can be treated or can benefit from a reduction in the absorption of nutrients (e.g., glucose) that can be achieved by generating a barrier that decreases absorption of the nutrients by the tissue as described herein.

The hydratable compositions described herein can be used to deliver biologically active substances such as biomolecules. The term "biomolecules," as used herein, refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, neutraceuticals, small molecules, cytokines, cell response modifiers such as growth factors and chemotactic factors, antibodies, vaccines, haptens, toxins, interferons, ribozymes, antisense agents, plasmids, DNA, and RNA. In some embodiments, the biologically active substances include gene editing agents, bacteria (to alter microbiome), viruses, antibiotics, shRNA, and aptamers. In some embodiments, these biologically active substances are capable of being released at site of action. In some embodiments, these biologically active substances are biologically active at the site of action.

In some embodiments, the average number of aluminum ions per molecule in the composition is less than 40, 30, 20, or 10. In some embodiments, the composition is capable of forming a paste following contact with an aqueous liquid with a pH greater than 6, 7, 8, 9, or 10.

The terms "polynucleotide," "nucleic acid," or "oligonucleotide" refer to a polymer of nucleotides. The terms "polynucleotide," "nucleic acid," and "oligonucleotide," may be used interchangeably. Typically, a polynucleotide comprises at least three nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5 bromouridine, C5 fluorouridine, C5 iodouridine, C5 methylcytidine, 7 deazaadenosine, 7 deazaguanosine, 8 oxoadenosine, 8 oxoguanosine, O(6) methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5"-N phosphoramidite linkages).

As used herein, a "polypeptide," "peptide," or "protein" comprises a string of at least three amino acids linked together by peptide bonds. The terms "polypeptide," "peptide," and "protein" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain; see, for example, as described on the world-wide-web at cco.caltech.edu/ ~dadgrp/ Unnatstruct.gif, which displays structures of non-natural amino acids that have been successfully incorporated into functional ion channels) and/or amino acid analogs as are known in the art may alternatively be employed.

Also, one or more of the amino acids may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

The terms "polysaccharide," "carbohydrate," or "oligosaccharide" refer to a polymer of sugars. The terms "polysaccharide," "carbohydrate," and "oligosaccharide," may be used interchangeably. Typically, a polysaccharide comprises at least three sugars. The polymer may include natural sugars (e.g., glucose, fructose, galactose, mannose, arabinose, ribose, and xylose) and/or modified sugars (e.g., 2'-fluororibose, 2'-deoxyribose, and hexose).

The term "humectant" refers to a substance that absorbs or helps another substance retain moisture, such as a hygroscopic substance. It has the property to promote water retention in a substance. When incorporated into a compound structure, hydrophilic humectant molecules increase efficacy of hydration. A crosslinking humectant is an effective cross-linker or spacer that connects different components of a compound or composition.

The hydratable compositions described herein may contain one or more therapeutic, prophylactic, and/or diagnostic agents that are released. The agent may be a small molecule agent (e.g., molecular weight less than 2000, 1500, 1000, 750, or 500 amu), a macromolecule, or a biomolecule (e.g., peptide, protein, enzyme, nucleic acid, polysaccharide, mRNA, siRNA, growth factors, cell adhesion sequences (e.g., RGD sequence, integrins), extracellular matrix components), or combinations thereof. The agent may also be a vaccine.

Exemplary classes of small molecule agents include, but are not limited to, anti-inflammatories, analgesics, antimicrobial agents, steroids, stem cell activating molecules, regenerative therapeutics, and combinations thereof.

Exemplary cytokines and growth factors include, without limitation, TNF, TGF-b, acidic fibroblast growth factor, basic fibroblast growth factor, chemokines such as SDF-1, epidermal growth factor, IGF-I and II, vascular endothelial-derived growth factor, bone morphogenetic proteins, platelet-derived growth factor, heparin-binding growth factor, hematopoietic growth factor, and peptide growth factor. Exemplary extracellular matrix components include, but are not limited to, collagen, fibronectin, laminin, elastin and combinations thereof. Proteoglycans and glycosaminoglycans can also be covalently or non-covalently associate with the materials described herein.

The hydratable compositions described herein may also be used as a vehicle to deliver cells and/or transfection agents.

The hydratable compositions described herein may be applied via multiple modalities including direct application, endoscopy, needle, brush, spray, plug, pill, tablet and gel-cap.

In some embodiments, the particulate, e.g., microparticulate, hydratable compositions described herein are not absorbed by the body of the patient to whom they are administered.

In some embodiments, the hydratable compositions can be formulated as a powder, emollient, cream, ointment or suspension.

In some embodiments, the paste, which is obtained by contacting the hydratable composition with a liquid containing water, can be used to coat biological surfaces, e.g., the rectum, vagina, nasal, and skin.

In some embodiments, the hydratable composition can be delivered as a drink, a solution, or an elixir. In some embodiments, the composition can be administered in a drinking straw form.

In some embodiments, the hydratable composition can be used to deliver sensing molecules (e.g., sensors) as well as contrast agents (e.g., microbubbles or radiocontrast agent).

The present disclosure also provides methods to treat topical wounds and burns by identifying a subject in need of such treatment, and applying the hydratable composition or the paste, which is obtained by contacting the hydratable composition with a liquid containing water, to the sites of topical wounds and burns. In some embodiments, the composition is in the form of cream.

In another aspect, the present disclosure also provides methods to promote mucosal healing by identifying a subject in need of such treatment, and applying the hydratable composition or the paste, which is obtained by contacting the hydratable composition with a liquid containing water, to the sites in need of such treatment.

In one aspect, the present disclosure also provides a method to treat dermatitis. The method includes the step of identifying a subject in need of such treatment, and applying the hydratable composition or the paste, which is obtained by contacting the hydratable composition with a liquid containing water, to the sites of dermatitis. Other uses are also contemplated, e.g., treating hemorrhoids, treating venous ulcers, treating infection, etc.

The term "subject" is used throughout the specification to describe an "animal" or a "human." The term "animal" includes, but is not limited to, birds, reptiles, amphibians, and mammals, e.g., humans, other primates, pigs, rodents such as mice and rats, rabbits, guinea pigs, hamsters, cows, horses, cats, dogs, sheep and goats. Preferred subjects are humans, farm animals, and domestic pets such as cats and dogs.

As used herein, the phrase "therapeutically effective amount" refers to the amounts of the hydratable compositions described herein that elicit the desired biological or medicinal response including: (1) inhibiting a disease, condition, or disorder, or one or more symptoms of the disease, disorder, or condition, in an individual who is experiencing or displaying the pathology or symptomatology of the disease, condition or disorder such as in the case of type 2 diabetes mellitus, inhibiting increased plasma glucose levels; (2) promoting weight loss; (3) preventing or reducing the risk of developing type II diabetes in a subject having pre-diabetes; or (4) ameliorating the disease or symptoms of the disease; for example, ameliorating a disease, condition, or disorder, or symptom thereof, in an individual who is experiencing or displaying the pathology or symptomatology of the disease, condition, or disorder (i.e., reversing the pathology or symptomatology) such as ameliorating plasma glucose levels.

For example, the following symptoms of diabetes can all be improved by treating a subject with the compositions described herein: ameliorating plasma glucose levels, HbA1c levels, plasma insulin levels, or active or total Glucogon-like peptide (GLP) levels, or eliminating increased thirst, frequent urination, increased hunger, hypertension, hyperlipidemia, weight loss or gain, obesity-related joint problems, high blood pressure, total cholesterol, elevated LDL and triglycerides, metabolic syndrome, fatigue, blurred vision, slow healing sores, frequent infections, neuropathic pain, kidney failure, or darkened skin AND/OR elicit one or more of the following: increased levels of postprandial active GLP-1 in plasma, decreased levels of postprandial glucose in plasma, increased levels of C-peptide in plasma, decreased levels of appetite sensation measured by Visual Analogue Scale (VAS), decreased levels of 24-hour plasma glucose assessed by Continuous Glucose Monitoring System (CGMS) or weight loss.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The term "kit" refers to pharmaceutical kits useful, for example, in the treatment or prevention of diabetes or obesity, which include one or more containers containing a compound or pharmaceutical composition comprising a therapeutically effective amount of one or more of the compounds described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The term "polymer" is employed herein to refer to chemical compounds or a mixture of compounds comprised of repeating structural units.

The phrase "mucoadhesion" is employed herein to refer to a form of adhesion between two materials, at least one of which is a mucosal surface. Mucoadhesion typically occurs within the body of a subject.

The phrase "oral glucose tolerance test" refers to a diagnostic assay in which blood samples are obtained from a subject or patient following glucose administration to determine time to clearance of the glucose from the subject's or patient's system. The test is commonly utilized in determining the presence of diabetes or insulin resistance in a subject or patient.

The term "hydratable composition," "water hydratable composition," or "water-based liquid hydratable composition" refers to a composition that can form a paste following contact with a liquid containing water, e.g., pure water, or an aqueous solution with one or more solutes. The liquid can have any pH, for example, it can be acidic, or non-acidic, e.g., it can have a pH value from 1 to 14.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is a schematic diagram depicting the concept of oral delivery of the new sulfated agent-based hydratable compositions (AF-LuCI particles), e.g., in a pill or a capsule, that are dispersed to form a barrier coating in the gastrointestinal tract, e.g., in the stomach and/or small intestines.

FIGS. 4A and 4B are schematic representation of the chemical changes of poly aluminum complex (PAC) in sucralfate and AC-LuCI during fabrication.

FIG. 19A is a graph showing reduction of glucose responses in incremental Area Under the Curve (iAUC) of Sprague Dawley (SD) rats gavaged with AF-LuCI pastes in different viscosities and doses.

FIG. 19B is a graph showing correlation between the AF-LuCI viscosity in two different doses (450 and 2,700 mg/kg) and iAUC.

FIG. 19C is a graph showing percentage reduction of iAUC in oral glucose tolerance test (OGTT) with different AF-LuCI dosing schedule.

FIG. 19D is a schematic diagram showing local barrier effect of AF-LuCI in OGTT with orally administered glucose.

FIG. 19E is a graph showing OGTT curves of rats gavaged with AF-LuCI pastes. Rats gavaged with 0.9 w/v % normal saline was used as a control.

FIG. 19F is a graph showing iAUC of the OGTT curves in FIG. 19E. (*<0.05 and **<0.001 in one-way Analysis of Variance (ANOVA)).

FIG. 19G is a schematic diagram showing representative schematic of no systemic effect of AF-LuCI in intraperitoneal injection (IpGTT) with systemically administered glucose.

FIG. 19H is a graph showing IpGTT curves of rats gavaged with AF-LuCI pastes. Rats gavaged with 0.9 w/v % normal saline was used as a control.

FIG. 19I is a graph showing iAUC of the OGTT curves in (h). (*<0.05 and **<0.001 in one-way ANOVA)

DETAILED DESCRIPTION

Figure 2:
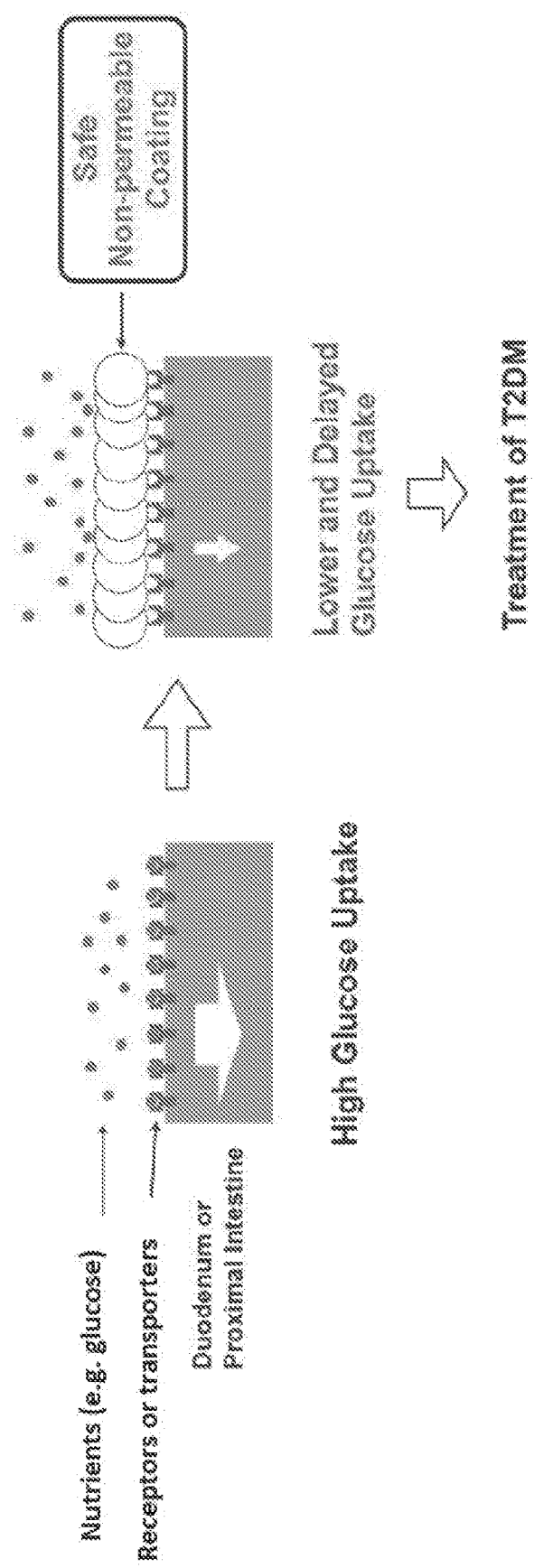
FIG. 2 is a schematic diagram showing the dispersal of the dry particles in the presence of liquids within the stomach and/or small intestines and instantly forming a safe, non-permeable barrier coating on the stomach and/or intestinal lining that can reduce and/or delay the uptake of glucose and other nutrients.

The present disclosure describes methods of altering nutrient exposure via coating of the luminal surface of portions of the GI tract (e.g., proximal GI tract) including the proximal intestine with an orally administered mucoadhesive hydratable compositions, e.g., microparticulate, formulation, or a liquid formulation (see, e.g., FIG. 1). These hydratable compositions are made of particles that include aluminum cross-linked sulfated agents, such as sucralfate, which is a sucrose octasulfate-aluminum complex that is an FDA-approved, orally administered drug indicated for the treatment of active gastric and duodenal ulcers. The viscosity of sucralfate is a key determinant of its barrier performance. When exposed to an aqueous liquid (i.e., stomach acid or intestinal fluid), the hydratable compositions form a sticky paste that physically coats the luminal surface of the mouth, throat, stomach, duodenum, and/or small intestines to thicken the protective mucosal layer via a strong mucoadhesive interaction with gastric and duodenal mucus (S. Higo et al; Pharm. Res. 21, 413-419 (2004); Tasman-Jones and Morrison, Am. J. Med., 86, 5-9 (1989); Slomiany et al., Am. J. of Med., 91, 30-36, 1991).

However, when sucralfate is used by itself and reacts with stomach acid to form a sticky paste, it releases a significant amount of aluminum. Hence, one hurdle for the use of sucralfate for the treatment of T2DM is potential excessive aluminum absorption, particularly due to the fact that a prolonged, repeated dosing required for T2DM therapy, leading to long-term aluminum exposure. Further, 25-40% of diabetic patients suffer from chronic renal impairment and hence, may be increasingly susceptible to potential side effects due to the aluminum release from sucralfate. Unlike patients with normal renal function who can adequately excrete the aluminum and hence only retain a limited quantity, patients with CRI can have an impaired excretion of aluminum that could limit the long-term use of sucralfate for T2DM patients (J. P. New et al., Diabetic Medicine, 24, 364-369; Eberhard, Ritz et al., New Engl. J. Med., 341, 1127-1133(1999)). Thus, it is essential to ensure that transient nutrient barrier coatings that are to be administered over prolonged periods of time release little to no toxic components such as aluminum. Reducing the exposure of aluminum to a T2DM patient would increase the safety profile of this therapy for clinical translation of sucralfate as an intestinal barrier in patients.

Sucralfate has also been used to prepare sucralfate compositions, e.g., as described in PCT WO2014/151565, which is incorporated herein by reference. While prior sucralfate compositions exhibit an effective barrier property to glucose absorption when rehydrated in acidic liquids, a significant quantity of sucralfate is liberated during gelation after rehydration, and thus the full amount of the composition not available for subsequent coating. Furthermore, during the initial rehydration process, the compositions release aluminum. This released aluminum can potentially accumulate in tissue over time with repeated exposures, which can be highly undesirable and is specifically contraindicated in patients with renal insufficiency.

Ideal mucoadhesive formulation for gut coating should 1) be capable to form a layer on mucus layer on the lumen upon contact with aqueous mucus on different segments of GI tract with different pH (i.e. stomach pH~1, duodenum pH 3-5, intestine pH>6), 2) have good barrier properties, 3) be stable in shear stress under aqueous environment (i.e. shear resistance, low swelling), 4) be able to be encapsulated into enteric coated capsules, thus should be in dried formulation, 5) be safe to use.

Commonly used gelatinous mucoadhesive polymers are not suitable for this purpose given that they absorb water and swell rapidly that can compromise the mucoadhesion, shear resistance and the barrier properties. In the screening result in our earlier study, sucralfate has been identified as having the best barrier properties. In stomach acid, sucralfate forms a sticky paste that can bind to stomach ulcers to form a protective layer. However, given that sucralfate requires acid (pH lower than ~2) to form the sticky paste and the binding is specific to ulcers, it is undesirable to form a layer on duodenum or intestine with higher pH environment.

Hence, as described herein, new mucoadhesive particle compositions were developed based on sucralfate and other sulfated agents that can form a mucoadhesive sticky paste that provides a barrier coating of the gut and that simultaneously minimize the potential side effects by reducing the amount of aluminum content released into the body.

A surprising benefit realized for the new hydratable compositions is that they can be rehydrated in liquids at any pH, and thus can be used to form viscous coatings not only in the stomach, but also in other parts of the GI tract, e.g., in the stomach (pH 1), duodenum (pH 3-5), intestine (pH 6-7), and colon (pH 5.5-7). The new methods described herein can significantly reduce the water content below the levels found in prior sucralfate compositions, which enables the new hydratable compositions to be rehydrated with aqueous liquids, such as water, regardless of pH, and without altering PAC chemistry or without using any additives (gel protector agents, humectants, etc.). As a result, one can deliver more of the hydratable composition per unit volume in a given pill, tablet, or capsule than is possible for prior sucralfate compositions with a higher water content.

In some embodiments, the new hydratable compositions can form a paste following contact with a liquid having any pH, for example, pH 1, pH 2, pH 3, pH 4, pH 5, pH 6, pH 7, pH 8, pH 9, pH 10, pH 11, pH 12, pH 13, or pH 14. In some embodiments, the liquid can have a pH from 1 to 14, from 2 to 13, from 3 to 12, from 4 to 11, from 5 to 10, from 6 to 9, from 6 to 10, from 6 to 11, from 6 to 12, from 6 to 13, or from 6 to 14; or have a pH greater than 6, 7, 8, 9, 10, 11, 12, or 13.

General Methodology

The novel aluminum-crosslinked sulfated agent-based, e.g., sucralfate-based, hydratable compositions are inert, non-absorbable compositions in the form of dried particulates or suspensions that can temporarily coat the luminal lining of the digestive track and reduce absorption of ingested nutrients through the intestinal lining and thus keep those blocked nutrients from entering into the blood stream or having other systemic effects.

The examples below demonstrate that the administration of the new particulate, e.g., microparticulate, compositions described herein provide an effective barrier to glucose absorption anywhere in the GI tract, e.g., to thereby lower postprandial blood glucose concentration. Thus, the new compositions and methods can be useful to treat disorders in which one desires to reduce the absorption of one or more nutrients into the body.

For example, management of type II diabetes requires an altered diet, often in addition to a drug or insulin-based therapy. Similarly, controlling various forms of obesity require regulation of food intake together, often with drug therapy or surgical approaches including bariatric surgery. As shown schematically in FIG. 2, the sulfated agent-based hydratable compositions described herein reduce nutrient passage from the intestinal lumen to the blood stream through the intestinal lining. For example, inhibition or delayed inhibition of nutrient absorption can mean inhibiting glucose absorption. Thus, the new hydratable compositions can be used to treat type II diabetes.

The hydratable compositions described herein are prepared in a manner to reduce the presence of metallic ions (i.e., aluminum ion) in the compositions to thereby reduce the release of aluminum from the sucralfate based hydratable composition in the presence of acid (i.e., stomach acid), in turn, reducing the potential side effects from excess aluminum in the bloodstream.

Hydratable Compositions and Methods of Making the Compositions

The aluminum-crosslinked sulfated agent-based, e.g., sucralfate-based, hydratable compositions (also referred to herein as "AF-LuCI" particles) include or consist of a polymer of ionized aluminum ions. Sucralfate is composed of aluminum hydroxides linked to sucrose octasulfate. Other sulfated agents include sulfated dextran, sulfated dextrin, sulfated amylopectin, sulfated amylose, sulfated cellulose, carrageenan, chondroitin sulfate, glucose sulfate, sucrose sulfate, heparin, heparin sulfate, and raffinose sulfate.

Sucralfate comprises two oppositely charged polyions forming a water-insoluble salt: anionic sucrose octasulfate, and cationic poly aluminum complex (PAC) (FIG. 4A). PAC is a cationic inorganic polymer with aluminum ions as backbone linked together via coordination bonds with hydroxo linkages (—OH—). When it is exposed to acid, a part of the hydroxo linkages are reversibly protonated to form water (—OH$_2$) and in stronger acid additional protonation (W) and further hydration (H$_2$O) irreversibly break the bond to shorten the polymer chain that is surrounded by more water molecules compared to the PAC in the native sucralfate (FIG. 4B).

Figures 4C, 4D:
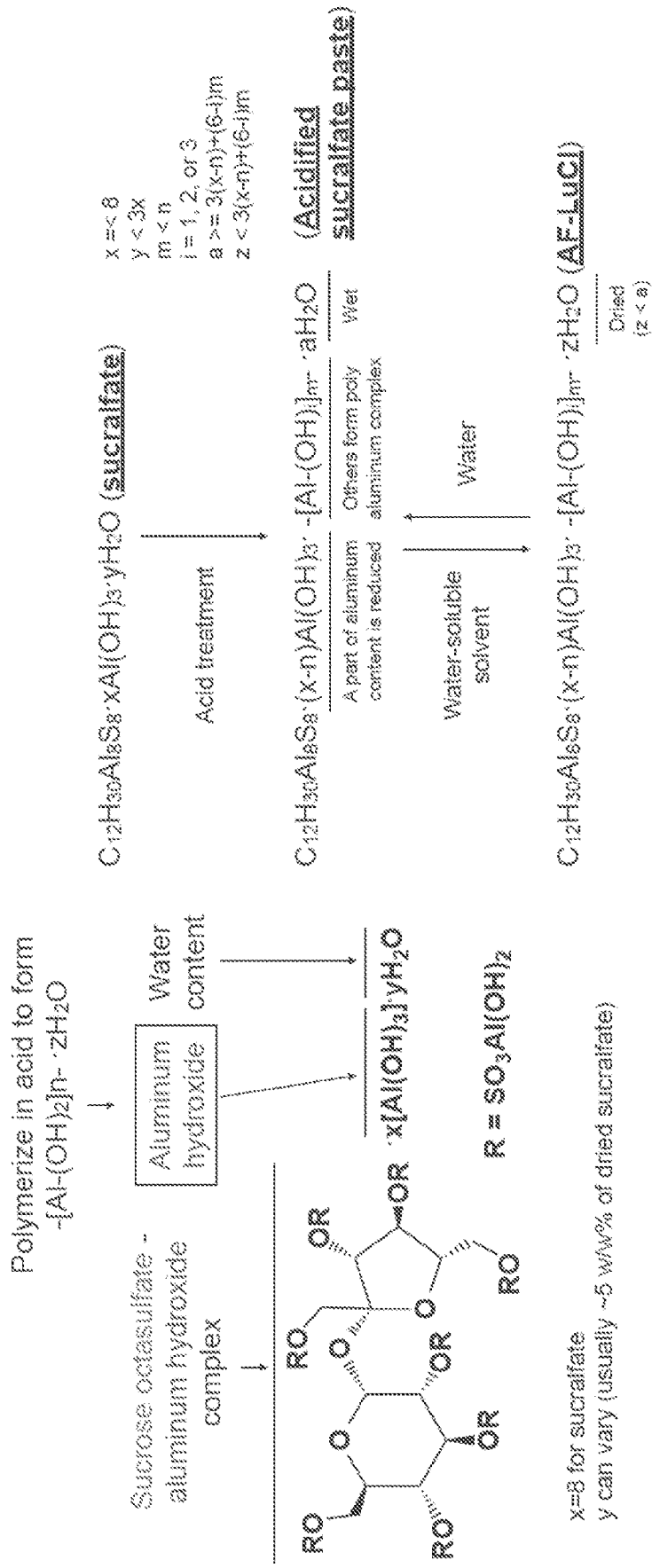
FIGS. 4C and 4D are representations of the chemical structures and chemical formulas of sucralfate, acidified sucralfate paste, and AF-LuCI. The ionized aluminum atoms (coordination number=6) are polymerized through coordination bonds with hydroxyl groups and surrounded by water molecules also through coordination bonds.

When a sulfated agent such as sucralfate reacts with an acid, a part of the aluminum component is released and another part cross-links together to form a "poly aluminum complex." The ionized aluminum atoms (coordination number=6) are believed to be polymerized through coordination bonds with hydroxyl groups and surrounded by water molecules also through coordination bonds. As shown in FIG. 4C, when the aluminum hydroxide groups react with acid they form partially hydrated cationic poly-aluminum complexes. The hydrated poly-aluminum complex has an overall positive charge and strongly binds to negatively charged sucrose octasulfate through electrostatic interactions to form a water-insoluble sticky paste. As the hydroxo linkages are responsible for the pH-dependent change of rheological properties by reversible protonation, the shorter PAC polymers with less hydroxo linkages and more bound water (—OH$_2$) would minimize the pH-dependency and can be easily dehydrated/re-hydrated without the need of acid. In addition, by controlling the electrostatic charge, the shorter and more hydrated PAC polymers would undergo complex coacervation with anionic sucrose octasulfate where the two polyions are electrostatically entangled to form a water-immiscible liquid with controlled viscosity.

Figure 3:
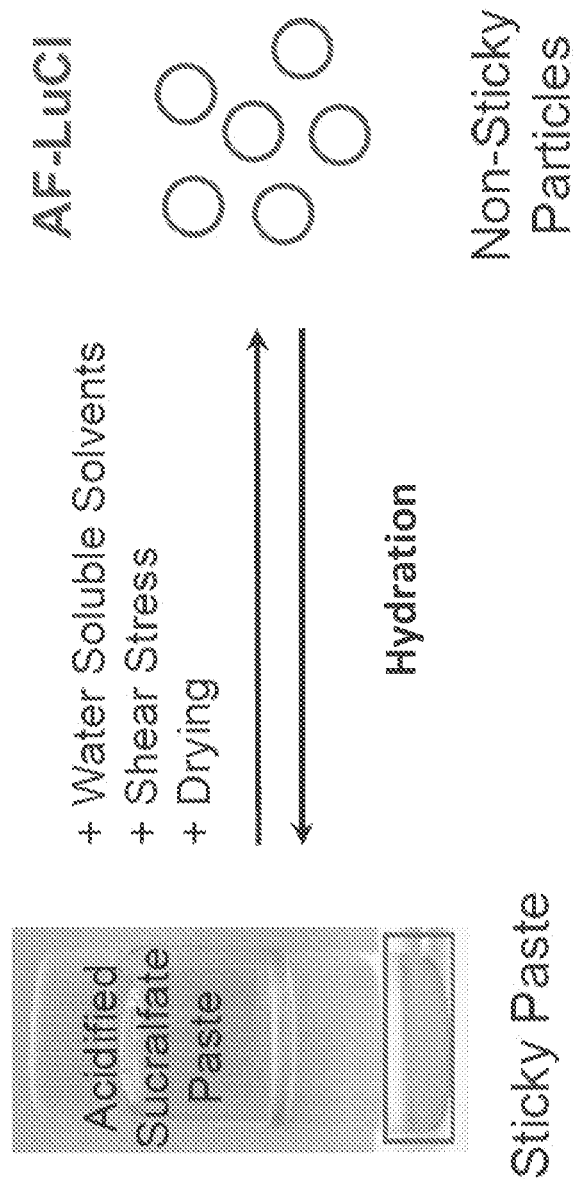
FIG. 3 is a schematic diagram showing how a sticky acidified sucralfate paste can be easily reformulated into non-sticky particles of AF-LuCI using water-soluble solvents.

Based on thermogravimetric analysis (TGA) and Fourier-transform infrared spectroscopy (FT-IR) as described in the examples below, and without being bound by the following theory, in the example using sucralfate, as shown in FIGS. 3 and 4D, it appears that when the acidified sucralfate sticky paste is mixed with a water-soluble (water-miscible) solvent such as alcohol (and then the solvent is removed), a rapid dehydration reaction occurs and a number "n" of the x aluminum hydroxide groups (Al(OH)$_3$) of sucralfate leave the structure (leaving "x–n"), and a number "m" of aluminum hydroxide groups appear to form a poly-aluminum complex that is crosslinked via 1 or 2 or 3 hydroxyl groups (—OH)$_i$)(where i=1 or 2 or 3) between the aluminum ions to form —[Al—(OH)$_i$]$_m$. Therefore, the predicted chemical structures of sucralfate, acidified sucralfate paste, and AF-LuCI are:

$C_{12}H_{30}Al_8S_8 \cdot xAl(OH)_3 \cdot yH_2O$ (sucralfate)

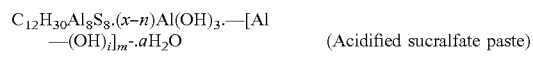

$C_{12}H_{30}Al_8S_8 \cdot (x-n)Al(OH)_3 \cdot -[Al-(OH)_i]_m \cdot aH_2O$ (Acidified sucralfate paste)

$C_{12}H_{30}Al_8S_8 \cdot (x-n)Al(OH)_3 \cdot -[Al-(OH)_i]_m \cdot zH_2O$ (AF-LuCI)

where x is less than or equal to 8 (8 for sucralfate, and is equal to the number of aluminum atoms), 0<n<x, m is greater than or equal to 2 (and can be less than n), and i=1 or 2 or 3.

The variable y in yH$_2$O is the moisture that is absorbed and potentially complexed with Al. Therefore, y<(6-3)x=3x, where 3x denotes the maximum number of water molecule that can bind to Al(OH)$_3$. The variable z is also the absorbed moisture in AF-LuCI. Therefore, z<3(x–n)+(6–i)m, where (3(x–n) is the maximum number of water molecules that can bind to Al(OH)3, and (6–i)m is that for the poly aluminum complex. Note that the "y" and "z" "H$_2$O" values can range from 5.0-40.0 w/w % in sucralfate, e.g., can be less than 20 w/w %.

In general, to fabricate the dry AF-LuCI particles using solvent-based dehydration, a sulfated agent, such as sucralfate, is first treated with an acid solution (e.g., 0.1-1.0 N HCl solution) to form a viscous precipitate ("sticky paste") (as shown schematically in FIG. 3). The precipitate is then rapidly dehydrated, e.g., by mixing with a sufficient amount, e.g., at least 30 v/v %, of a water-soluble (water-miscible) solvent (but not a water-immiscible solvent) and mixed to apply a shear stress for a time sufficient to obtain a particle suspension, e.g., from a few seconds to a few minutes, and then removing the solvent. In some embodiments these particles can be white.

In some embodiments, the viscous sticky paste is further combined with water-soluble solvents (e.g., alcohol, acetone, DMSO, DMF, etc.) and vortexed resulting in a white particle suspension. The suspension is then dried to remove the solvent and the dried particles are further ground to form a white powder.

In some embodiments, the acid solution is hydrochloric acid (HCl), hydroiodic acid (HI), hydrobromic acid (HBr), perchloric acid (HClO$_4$), nitric acid (HNO$_3$) or sulfuric acid (H$_2$SO$_4$). In some embodiments, the acid solution is 0.1 N HCl, 0.2 N HCl, 0.3 N HCl, 0.4 N HCl, 0.5 N HCl, 0.6 N HCl, 0.7 N HCl, 0.8 N HCl, 0.9 N HCl, or 1.0 N HCl. In some embodiments, the hydrochloric acid (HCl) has a concentration greater than 0.1N, 0.2 N, 0.3 N, 0.4 N, 0.5 N, 0.6 N, 0.7 N, 0.8 N, 0.9 N, or 1.0 N.

Useful water-soluble solvents include alcohols (e.g., methanol, ethanol, isopropanol, n-propanol, reagent alcohol, 2-butoxiethanol, and furfuryl alcohol), acetone, dimethyl sulfide (DMSO), N,N-dimethyl formamide (DMF), acetonitrile, 1,4-dioxane, tetrahydrofuran (THF), acetic acid, acetaldehyde, 1,2-butandiol, 1,3-butandiol, 1,4-butandiol, butyric acid, diethanolamine, diethylenetriamine, dimethoxyethane, ethylamine, ethylene glycol, formic acid, glycerol, methyl diethanolamine, methyl isocyanide, 1,3-propanediol, 1,5-pentanediol, propanoic acid, propylene glycol, pyridine, and triethylene glycol.

In another embodiment, instead of using water-soluble (water-miscible) solvents to quickly dehydrate the acidified sucralfate paste, one can also use other quick dehydration methods, e.g., to quickly heat and dry the composition, e.g., with a microwave oven, to prepare AF-LuCI particles. For example, an amount of a sulfated agent, such as sucralfate, can be added to a container, e.g., a glass vial, and then mixed with an acidic solution, e.g., an amount, e.g., 10 ml, of 0.1-1.0 N HCl solution in water, and immediately vortexed in 3000 rpm for 10 seconds to form a viscous precipitation. For example, a microwave drying process can be performed with a microwave oven (power: 800 W) for 30 seconds.

The particles from which the solvent is removed can be further dried to remove any remaining water-soluble solvent. The dried particles can be ground or crushed to form even smaller particles to form a AF-LuCI powder.

The dried particles or powder can then be rehydrated as needed in any aqueous liquid regardless of pH. The resulting viscous sticky paste, or the particles or powder, can be mixed with various agents to stabilize the paste or particles and to control the level of hydration and control overall viscosity. For example, those agents can include humectants or cross-linking humectants. These agents can include, consist of, or consist essentially of, e.g., carrageenan, propylene glycol, 1,2,6-hexanetriol, butylene glycol, dipropylene glycol, hexylene glycol, glycerin, triethylene glycol, erythritol capryl glycol, phytantriol, hexanediol beeswax, hexanetriol beeswax, panthenol, sodium pyrollidone carboxylic acid, hyaluronic acid, inositol, glycogen, sorbitol, polyglyceryl sorbitol, glucose, fructose, xylitol, elastin, collagen, silk, keratin, isoceteth, isolaureth, laneth, laureth, steareth, polyethylene glycol, silicon copolymers, ammonium lactate, glyceryl triacetate, hydrolyzed collagen, hydrolyzed elastin, hydrolyzed keratin, hydrolyzed silk, lactic acid, manitol, panthenol, polydextrose, propylene glycerol, quilaia, urea, or betaine.

Particle stabilizers can be selected, for example, from the non-limiting group of phosphate ions, pectin, carrageenan, chitosan, cellulose derivatives, gellan gum, alginate, gum karaya, dextran, pullulan, polyethylene glycol (PEG), polyvinyl alcohol (PVA) beeswax, sodium borate, stearic acid, carbomer, cetyl alcohol, propylene glycol, polysorbate, lecithin, glyceryl monostearate, acetic esters of fatty acid, lactic esters of fatty acid, citric esters of fatty acid, tartaric esters of fatty acid, acetyltartaric esters of fatty acid, sucroglycerides, polyglycerol esters of fatty acid, propane-2,3-diol esters of fatty acid, sodium stearoyl-2-lactylate, calcium stearoyl-2-lactylate, stearyl tartate, and castor oil derivatives.

Figure 5:
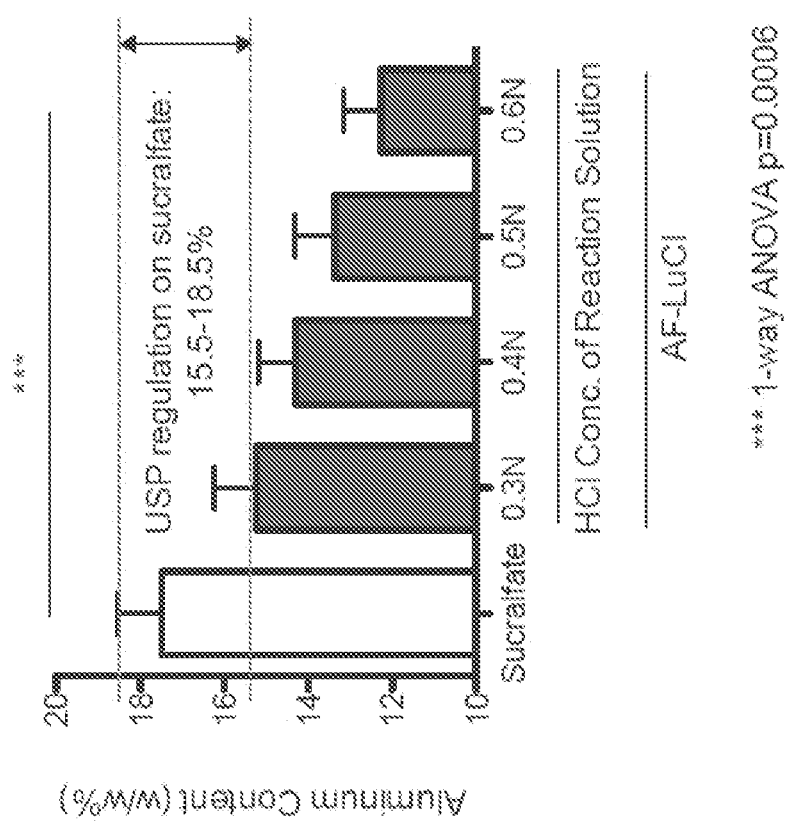
FIG. 5 is a bar graph showing the aluminum content of sucralfate vs. AF-LuCI particles. The AF-LuCI particles contain significantly lower aluminum content (lower than 15 w/w % of the total weight) compared to the native sucralfate (which is 15.5-18.5 w/w % of the total weight).

Because a part of aluminum content is released from sucralfate upon the acid treatment, the AF-LuCI particles have a significantly lower aluminum content (lower than 15.5 w/w % of the total weight, ranging from about 10.0 to about 15.5 w/w %) than the native sucralfate (USP regulation on the aluminum content of sucralfate is 15.5-18.5 w/w % of the total weight) (FIG. 5). As a result, the new hydratable compositions release a significantly lower level of aluminum compared to sucralfate and prior sucralfate compositions when rehydrated. For example, when sucralfate is used and exposed to an acidic fluid, e.g., gastric fluid, it releases about 15.0 w/w % of its original aluminum content. On the other hand, the new AF-LuCI hydratable compositions exposed to the same acidic fluid (or any aqueous liquid, regardless of pH) release less than about 2.0 w/w % of the original aluminum content of commercially available sucralfate.

In some embodiments, poly aluminum complex (PAC) polymers in AF-LuCI are shorter than in sucralfate, for example, the average number of aluminum ions per molecule of AF-LuCI can be less than 50, 40, 30, 20, 19, 18, 17, 16, 15, 14, 13, 12, 11, 10, 9, 8, 7, 6, or 5. In some embodiments, the numbers of aluminum ions per molecule of AF-LuCIs can be less than 40 or 30. In some embodiment, the average number of aluminum ions per molecule of AF-LuCIs can be about 20, 19, 18, 17, 16, 15, 14, 13, 12, 11, 10, 9, 8, 7, 6, or 5.

While sucralfate has been tested, other sulfated agents can also be used in the methods described herein. For example, sulfated agents including, but not limited to, sulfated dextran, sulfated dextrin, sulfated amylopectin, sulfated amylose, sulfated cellulose, carrageenan, chondroitin sulfate, glucose sulfate, sucrose sulfate, and raffinose sulfate, can be used to create the compositions described herein. In addition, all of the hydratable compositions described herein can be prepared by methods described herein using reagents that can be readily obtained from a commercial source. For example, sucralfate can be obtained from a commercial source such as Sigma-Aldrich (St. Louis, Mich.).

The dry particles, e.g., microparticles, described herein can be packaged into a pill, tablet, or capsule form. For example, the particles within any of the compositions described herein can be encapsulated by an enteric coating. For example, the coating can be comprised of one or more of gelatin, hydroxypropyl methylcellulose (HPMC), Eudragit®, and Acryl-EZE®. In some embodiments, the composition is a capsule containing the particles described herein. In addition, any of the hydratable compositions described herein can be mixed into a food substance (e.g., a bar or shake) or with other additives (e.g., a salt). Additional examples of food substances or additives are known in the art.

Methods of Using the Hydratable Compositions

The aluminum-crosslinked sulfated agent-based, e.g., sucralfate-based, hydratable compositions can be used to create an intestinal coating to inhibit nutrient absorption as a therapy or as an add-on therapy for patients with disorders that require reduction of ingested nutrients. T2DM patients exhibit increased blood glucose after ingesting glucose via routine food intake due to insulin resistance. Increased blood glucose levels lead to the classical symptoms of polyuria, polydipsia, and polyphagia. However, if left untreated, T2DM can lead to serious complications including ketoacidosis, hyperosmolar coma, cardiovascular disease, chronic renal failure, and retinopathy. Maintaining a healthy weight as a T2DM patient is an important life style factor to avoid increased severity of diabetes, increased complications, or even death. Hence, the use of a sucralfate-crosslinking humectant microparticulate by a T2DM patient would have dual benefits: reduction of glucose absorption, as well as reduction of absorption of other nutrients resulting in weight loss (e.g., fats and carbohydrates), and weight loss.

The decreased, or in some cases delayed, uptake of, for example glucose, could be a treatment for type II diabetes. In effect, it can lessen the dose needed for diabetes treatments including insulin, metformin, or sulfonylureas. The presence of the barrier particles resulting from the novel formulation forming a lining along the gastrointestinal tract can also modulate (e.g., decrease) the absorption of nutrients as the digested nutrients move through the intestine. The presence of the barrier particles creates a decreased surface area of the intestinal lining available to be in contact with digested nutrients and hence results in decreased or delayed absorption of such nutrients. The sucralfate based, hydratable compositions described herein are a potential therapy or add-on therapy for obesity, weight control, insulin resistance, hyperlipidemia, hypertension, and T2DM.

The duration of the sticky pastes formed by the new hydratable compositions in the GI tract is about 2-6 hours followed by degradation and excretion. However, the duration can be tailored to be shorter or longer based on viscosity and charge for specific compositions.

In other implementations, the new compositions can be used to carry other materials, such as drugs or antimicrobials. The release of the materials from the barrier layer can be controlled and can occur for an extended time period, yet is temporary. In another example, one can combine iodine, silver ions, and/or a chlorine-containing substance with the new compositions for attachment and slow release to inhibit the growth and/or proliferation of various microorganisms on surfaces, e.g., in the GI tract.

In any of the methods described herein, the subject is administered a dose of any of the compositions described herein For example, in any of the methods described herein the subject is administered a dose of any of the hydratable compositions described herein before eating (e.g., before eating a meal). The subject can be administered any of the compositions described herein between about 2 hours and about 1 minute (e.g., between 1.8 hours and 5 minutes, between 1.5 hours and 10 minutes, between 1.3 hours and 15 minutes, between 1.0 hour and 20 minutes, between 50 minutes and 25 minutes, or between 40 minutes and 25 minutes) before eating (e.g., before eating a meal). In other embodiments, the subject is administered any of the hydratable compositions described herein at substantially the same time as eating (e.g., while eating). The subject can be administered, e.g., one, two, three, four, five, six, or seven doses of any of the compositions described herein a day (e.g., over a total period of at least 1 month, at least 6 weeks, at least 2 months, at least 10 weeks, or at least 3 months). Some examples of the methods provided herein further include monitoring a subject's blood glucose levels and/or weight (e.g., before and after administration (e.g., repeated administration) of any of the compositions provided herein.

The hydratable compositions described herein may also be used as a vehicle to deliver cells and/or transfection agents. The hydratable compositions described herein may be applied via multiple modalities including direct application, endoscopy, needle, brush, spray, plug, pill, tablet and gel-cap. In some embodiments, the particulate, e.g., microparticulate, hydratable compositions described herein are not absorbed by the body of the patient to whom they are administered. In some embodiments, the hydratable compositions can be formulated as a powder, emollient, cream, ointment, or suspension.

In some embodiments, the paste that is obtained by contacting the hydratable composition with a liquid containing water, can be used to coat biological surfaces, e.g., the rectum, vagina, nasal, and skin. In some embodiments, the hydratable compositions can be delivered as a drink, a solution, or an elixir. In some embodiments, the compositions can be administered in a drinking straw form. See, for example, the world-wide-web at pharmaceuticalonline.com/doc/pediatric-drug-delivery-systems-drinking-straw-xstraw-0001.

In some embodiments, the hydratable composition can be used to deliver sensing molecules (e.g., sensors) as well as contrast agents (e.g., microbubbles or radiocontrast agent).

The present disclosure also provides methods to treat topical wounds and burns. The methods include identifying a subject in need of such treatment, and applying the hydratable composition or the paste, which is obtained by contacting the hydratable composition with a liquid containing water, to the sites of topical wounds and burns. In some embodiments, the composition is in the form of cream. A method of using sucralfate for treating topical wounds and burns is described in Beheshti, Akram, et al. "Comparison of topical sucralfate and silver sulfadiazine cream in second degree burns in rats." Adv Clin Exp Med 2013, 22, 4, 481-487 (2013), which is incorporated by reference in its entirety. In some embodiments, the composition includes silver sulfadiazine.

In another aspect, the present disclosure also provides a method to promote mucosal healing. The method includes the step of identifying a subject in need of such treatment, and applying the hydratable composition or the paste, which is obtained by contacting the hydratable composition with a liquid containing water, to the sites in need of such treatment. A method of using sucralfate to promote mucosal healing is described in Gupta, Pravin J., et al. "Topical sucralfate treatment of anal fistulotomy wounds: a randomized placebo-controlled trial." Diseases of the Colon & Rectum 54.6 (2011): 699-704, which is incorporated by reference in its entirety.

In one aspect, the present disclosure also provides a method to treat dermatitis. The method includes the step of identifying a subject in need of such treatment, and applying the hydratable composition or the paste, which is obtained by contacting the hydratable composition with a liquid containing water, to the sites of dermatitis. A method of using sucralfate to treat dermatitis is described in Markham, Trevor, Fionnuala Kennedy, and Paul Collins. "Topical sucralfate for erosive irritant diaper dermatitis." Archives of dermatology 136.10 (2000), which is incorporated by reference in its entirety.

Other uses are also contemplated, e.g., treating hemorrhoids, treating venous ulcers, treating infection, etc. Some of these uses, with compositions other than those described herein, are described in, e.g., WO1989005645A1, which is incorporated by reference in its entirety.

Pharmaceutical Formulations and Dosage Forms

Also within the scope of this disclosure are pharmaceutical compositions containing at least one hydratable composition described herein and a pharmaceutically acceptable carrier. Further, this disclosure covers methods of administering an effective amount of the compounds described herein, e.g., in a pharmaceutical composition, to a patient having T2DB or obesity, e.g., as described herein. "An effective amount" or "an amount effective" refers to the amount of a compound that is required to form a barrier on the lining of a portion or portions of the GI tract to confer a therapeutic effect on the treated patient. Effective doses will vary, as recognized by those skilled in the art, depending on the types of diseases treated, route of administration, excipient usage, and the possibility of co-usage with other therapeutic treatment.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Exemplary doses can range from about 5 g/day for an adult to a maximum dose of sucralfate of about 8 g/day for adult (~114 mg/kg for 70 kg adult). For the new hydratable compositions the dosages can be higher, from about 25 to about 50 g/day, with the potential to be administered in a liquid form, because of the significantly lower level of aluminum in the new compositions compared to sucralfate alone. In other examples, the dose can be between about 1 g/day to about 8 g/day (e.g., between 2 g/day to about 7 g/day).

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound described above. Examples of other carriers include colloidal silicon oxide, magnesium stearate, cellulose, sodium lauryl sulfate, and D&C Yellow #10.

The therapeutic compounds can also be prepared with carriers that will protect the therapeutic compounds against rapid elimination from the body, such as a controlled release formulation. Biodegradable, biocompatible polymers can be used, such as ethylene vinyl acetate, polyanhydrides, polyglycolic acid, collagen, polyorthoesters, and polylactic acid. The new compositions can be incorporated into controlled release formulations to modulate cranio-caudal distribution and retention time. Examples using such formulations are included below (examples 6 and 7). In addition, these formulations can be used to control the duration of the desired effects, for example, by altering the charge and/or viscosity of the overall formulation. In addition, the new compositions can be mixed with, e.g., "doped" with, additional drugs and can then be used as a drug delivery system.

Such formulations can be prepared using standard techniques, or obtained commercially, e.g., from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

Some compositions and pharmaceutical compositions can include a dry acid salt or a liquid acid salt (e.g., any of the exemplary dry acid salts or liquid acid salts described herein or known in the art). Such compositions and pharmaceutical compositions can be wetted with an aqueous solution before being administered to a subject or patient (e.g., administered to the small intestine of a subject).

The pharmaceutical compositions can be included in a container, pack, or dispenser together with instructions for administration.

Methods of formulating suitable pharmaceutical compositions are known in the art, see, e.g., the books in the series *Drugs and the Pharmaceutical Sciences: a Series of Textbooks and Monographs* (Dekker, N.Y.).

The compositions described herein can be preliminarily screened for their efficacy in treating above-described diseases by the whole-organism screening methods described herein and then confirmed by additional animal experiments and clinic trials. Other screening methods will also be apparent to those of ordinary skill in the art.

EXAMPLES

The invention described herein is a novel formulation of a polymer that can form a mucoadhesive layer on the intestinal wall, and hence act as a barrier to the absorption of digested nutrients traveling through the digestive tract. The invention is further described in the following examples, which do not limit the scope of the invention described in the claims.

Example 1—Method for Making a Hydratable Composition

The following method was used to fabricate an AF-LuCI particle composition that forms a viscous sticky paste in water without requirement of acid.

One gram of sucralfate (Heisen Pharmaceutical, China) was added in a 20 ml glass vial, added with 10 ml of 0.1-1.0N HCl solutions in water, and immediately vortexed in 3000 rpm for 10 seconds to form a viscous precipitation. The supernatant solution was removed and 10 ml of methanol, ethanol, isopropanol, or crude reagent alcohol was added. The vial was vortexed in 3000 rpm for 30 seconds to obtain a white particle suspension. The particles were precipitated using centrifugation (1000 rpm for 1 minute) or gravitational precipitation and the supernatant was removed.

In another test, instead of using solvents to dehydrate the acidified sucralfate paste, microwave-assisted drying was used to prepare AF-LuCI particles. One gram of sucralfate (Heisen Pharmaceutical, China) was added in a 20 ml glass vial, added with 10 ml of 0.1-1.0 N HCl solutions in water, and immediately vortexed in 3000 rpm for 10 seconds to form a viscous precipitation. The microwave drying process was performed with a microwave oven (power: 800 W) for 30 seconds.

The white particles were further dried using air-drying for more than 12 hours or under vacuum for at least 1 hour. The dried particles were ground using a mortar and pestle to formulate into white powders. The powders were stored in a closed glass vial in room temperature before use. The chemical status of sucralfate and AF-LuCI particles were evaluated using FT-IR (Bruker, measured from 500 cm-1 to 4000 cm-1 in wavenumber) and TGA (Perkin Elmer, measured from 20° C. to 800° C.). The key differences in prior sucralfate compositions (referred to herein as LuCI-X) and the new AF-LuCI particle fabrication methods are described in Table 1 below.

TABLE 1

| Formulation | LuCI-X particle | AF-LuCI Particle |
| --- | --- | --- |
| Particle fabrication | Acidified sucralfate paste is solidified in pH 7.4 and stabilized using phosphate ions to formulate into particles. | Acidified sucralfate paste is dehydrated using alcohol to formulate into particles. |
| Humectant requirement | A humectant (e.g., carrageenan) is required to form a paste in acid. | No humectant is required and capable to form a paste in any aqueous solutions. |
| Final drying | The final product is suspended in water (requires freeze-drying or long vacuum drying in high temperature). | The final product is suspended in volatile alcohol that can be easily dried. |

In one test, in solvent-based dehydration, the acidified sucralfate paste was added with excess amount of water-miscible common solvents (e.g., ethanol, methanol, dimethylsulfoxide (DMSO), acetone, etc.), and stirred to form a suspension in brittle particle form that is further dried in vacuum to evaporate solvents. In microwave-assisted dehydration, the acidified sucralfate paste was placed in a microwave oven, exposed to 1200 W microwave for 30 sec and ground into white powder using mortar and pestle. Briefly, to fabricate the dry particles using solvent-based dehydration, sucralfate was first treated with acid (0.3-0.8N HCl solutions) to form a viscous sticky paste that was further combined with water-soluble solvents (e.g., alcohol, acetone, DMSO, DMF, etc.) and vortexed resulting in a white particle suspension. The suspension was then dried to remove the solvent and the dried particles were further ground to form a white powder.

Example 2—Aluminum Content and Release from the Hydratable Compositions

Aluminum contents of sucralfate and AF-LuCI particles were measured using the colorimetric method recommended by USP. Briefly, about 1.0 g of sucralfate or AF-LuCI particle was transferred to a 250 mL volumetric flask, 10 mL of 6.0 N hydrochloric acid was added, mixed, and heated with continuous stirring in a water bath at 70° C. for 5 minutes. The solution was cooled to room temperature, diluted with water to volume, and mixed. The solution was filtered, discarding the first portion of the filtrate. Twenty-five milliliter of the filtrate was transferred to a 250 mL beaker, 25 mL of 0.05 M edetate disodium was added, 20 mL of acetic acid-ammonium acetate buffer was added, and mixed. The solution was heated in a water bath at 70° C. for 5 minutes. The resultant solution was cooled to room temperature, added with 50 mL of alcohol and 2 mL of dithizone, and mixed. The solution was then titrated with 0.05 M zinc sulfate until they form a bright rose-pink color. Each mL of 0.05 M edetate disodium consumed is equivalent to 1.349 mg of aluminum.

Because a part of aluminum content is released upon the acid treatment, the AF-LuCI contains significantly lower aluminum content compared to the native sucralfate (USP regulation on the aluminum content of sucralfate is 15.5-18.5 w/w % of the total weight). FIG. 5 shows the aluminum contents of sucralfate and AF-LuCIs. The AF-LuCI particles contain significantly lower aluminum content (lower than 15 w/w % of the total weight) compared to the native sucralfate (USP regulation on the aluminum content of sucralfate is 15.5-18.5 w/w % of the total weight).

Figure 6:
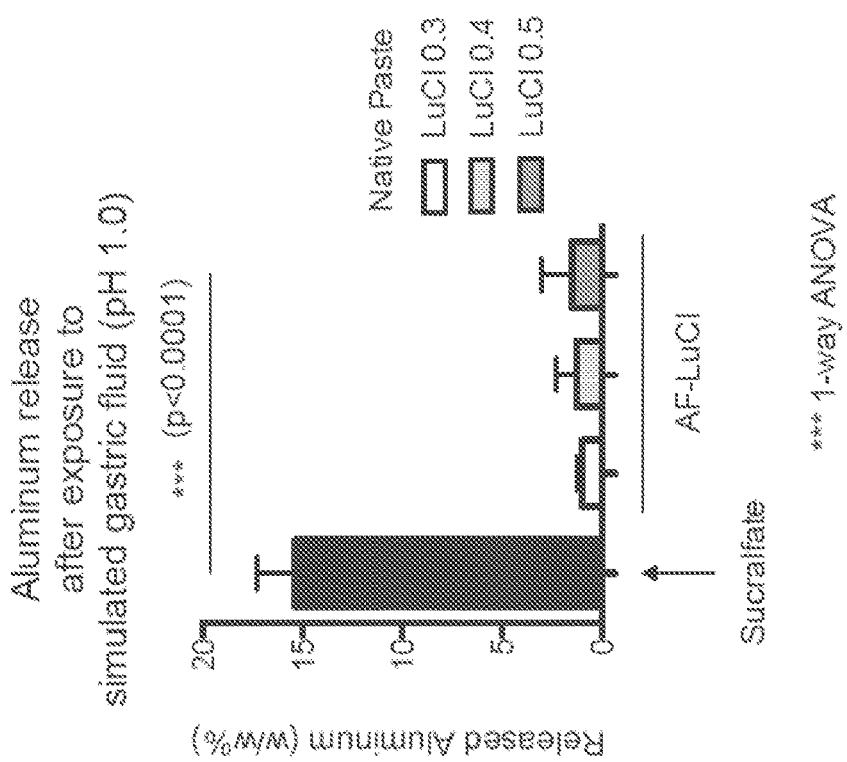
FIG. 6 is a bar graph showing the release of the aluminum components from sucralfate vs. AF-LuCI in simulated gastric fluid (simulated gastric fluid (SGF), pH 1.0).
Figure 7C:
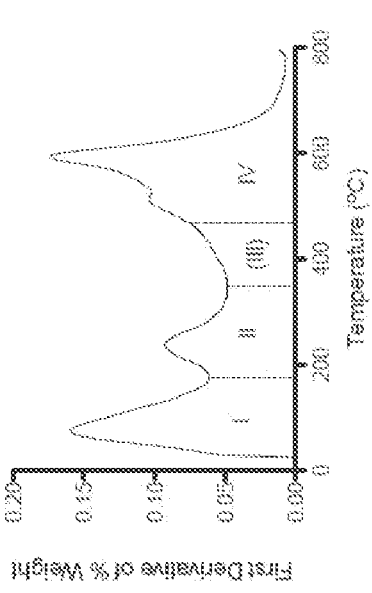
FIGS. 7A to 7D are a series of graphs that show thermogravimetric analysis (TGA) of sucralfate (thermal curve in FIG. 7A and first derivative curve in FIG. 7C) and AF-LuCI (thermal curve in FIG. 7B and first derivative curve in FIG. 7D) measured from 20° C. to 800° C.
Figure 7D:
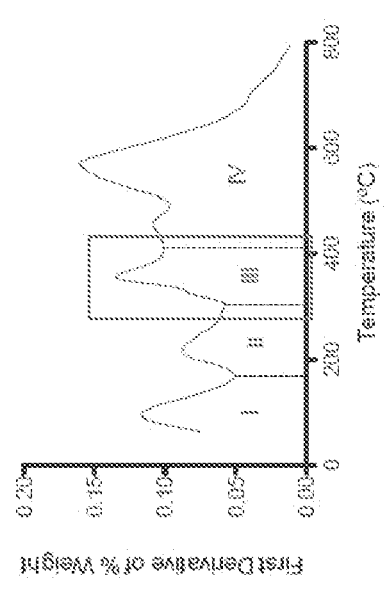
Figure 7A:
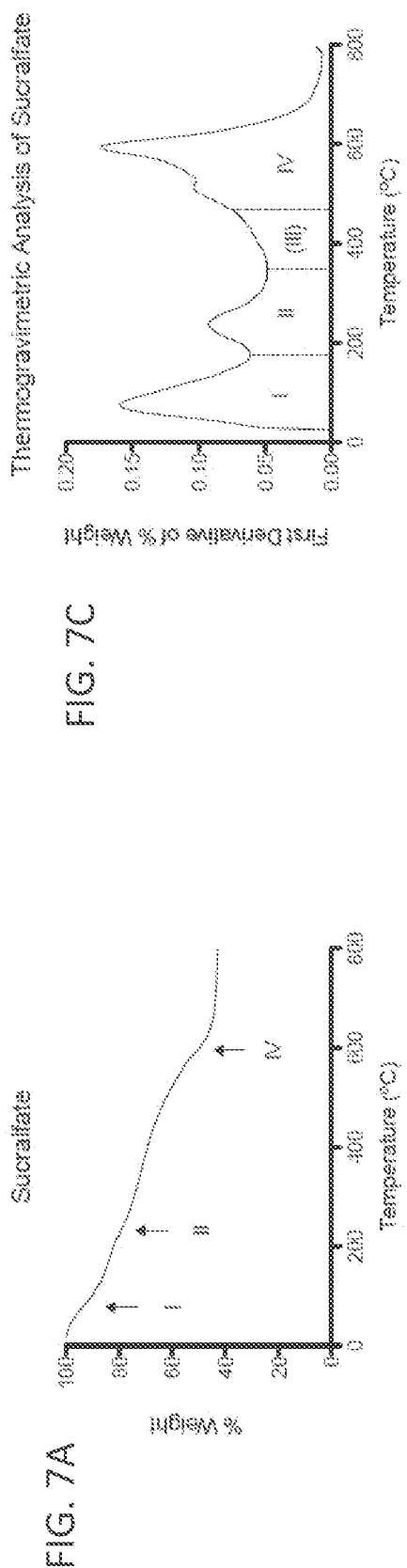
Figure 7B:
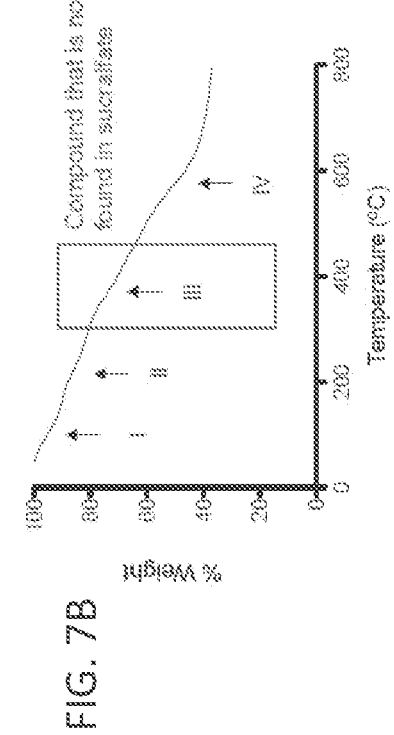

As shown in FIG. 6, when exposed to simulated gastric fluid (SGF, pH 1.0), the release of aluminum from AF-LuCIs was significantly lower (less than 2 w/w % of total aluminum content of AF-LuCI particle) compared to sucralfate (15 w/w % of total aluminum content of sucralfate). Moreover when exposed to simulated duodenal fluid (SDF, pH 3.5) or simulated intestinal fluid (SIF, pH 6.5), the aluminum release from AF-LuCI was undetectable using the colorimetric methods suggesting the enhanced safety for long-term use.

Example 3—Thermogravimetric Analysis (TGA) and Fourier Transform-Infrared (FT-IR)

The chemical composition was further evaluated in detail using thermogravimetric analysis (TGA) and the Fourier Transform-Infrared (FT-IR). As shown in FIGS. 7A-D, the TGA thermal curve of AF-LuCI showed a distinctive weight loss at 340-400° C. that was not found in the thermal curve of sucralfate suggesting that AF-LuCI has a component (i.e. poly aluminum complex) that does not exist in sucralfate. In particular, FIG. 7 shows the thermogravimetric analysis (TGA) thermal curve of (7a) sucralfate and (7b) AF-LuCI measured from 20° C. to 800° C. (c-d). The first derivative curves of (7c) graph (7a) (sucralfate) and (7d) graph (7b) (AF-LuCI) were also shown for clearer distinction of each segment. The TGA thermal curve of AF-LuCI showed a distinctive weight loss at 340-400° C. that was not found in the thermal curve of sucralfate suggesting that AF-LuCI has a component (i.e. poly aluminum complex) that does not exist in sucralfate.

Figure 8:
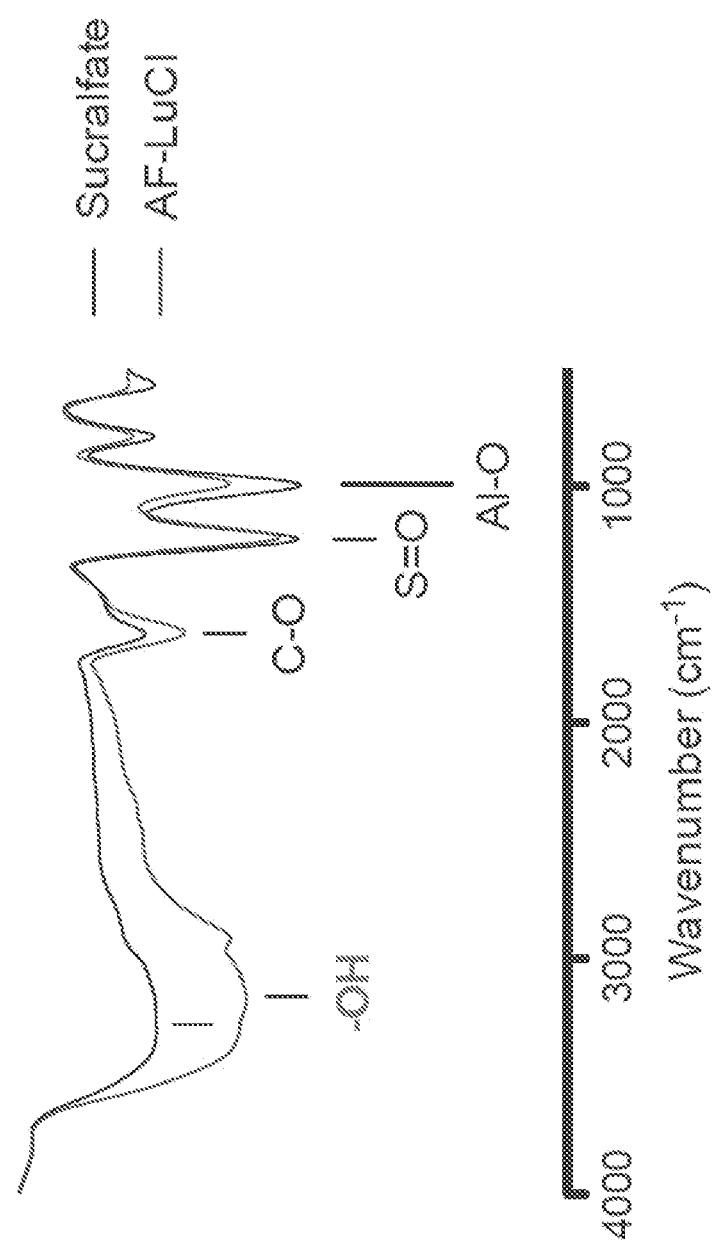
FIG. 8 is a representation of FT-IR spectra of sucralfate and AF-LuCI. The spectrum of AF-LuCI has a broad peak for —OH stretching at 3174 cm' whereas sucralfate has a broad peak for —OH stretching at 3312 cm' suggesting the —OH is in lower energy state indicating the —OH is more strongly bound to aluminum ions in poly aluminum complex compared to the —OH bound in aluminum hydroxide (Al(OH)3) in sucralfate.

The relatively high temperature for the weight loss of AF-LuCI (340-400° C.) compared to the thermal oxidation of aluminum hydroxide ($Al(OH)_3$) in sucralfate indicates that the new component in AF-LuCI requires higher energy to get oxidized supporting the presence of poly aluminum complex. In addition, as shown in FIG. 8, the FT-IR spectrum of the AF-LuCI showed a broad peak for —OH stretching at 3174 $cm^{-1}$ whereas sucralfate has a broad peak for —OH stretching at 3312 $cm^{-1}$ suggesting the —OH is in lower energy state indicating the —OH is more strongly bound to aluminum ions in poly aluminum complex compared to the —OH bound in aluminum hydroxide (Al(OH)$_3$) in sucralfate. Interestingly, FT-IR spectra of the paste formed by hydration of AF-LuCI and the acidified sucralfate pastes were closely similar indicating that they have similar chemical structures when they are hydrated to form paste in GI tract.

Example 4—Viscosity Measurements of AF-LuCI Hydratable Compositions

The mechanical properties of 1 w/v % material solutions in simulated stomach gastric fluid (SGF) were analyzed using a rheometer (AR-G2, TA Instruments). The dynamic viscosity of each material solution was measured using a 20 mm plate with 200 µm gaps (shear rate: 0.01-100 l/s in log scale, shear rate of 1 l/s was selected to compare viscosity of materials).

When the fabricated dry AF-LuCI particles were exposed to water, they rapidly formed a viscous sticky paste that had similar viscosity with the acid-treated sucralfate paste. This paste formation process had a few aspects that are quite distinct from the paste formation process of sucralfate, and that are clearly beneficial to form a coating layer in contact with wet surface (i.e. luminal surface of gut). The AF-LuCI particles could form the viscous sticky paste in all the pH that can be found in GI tract (i.e. pH 1-7).

Figure 9:
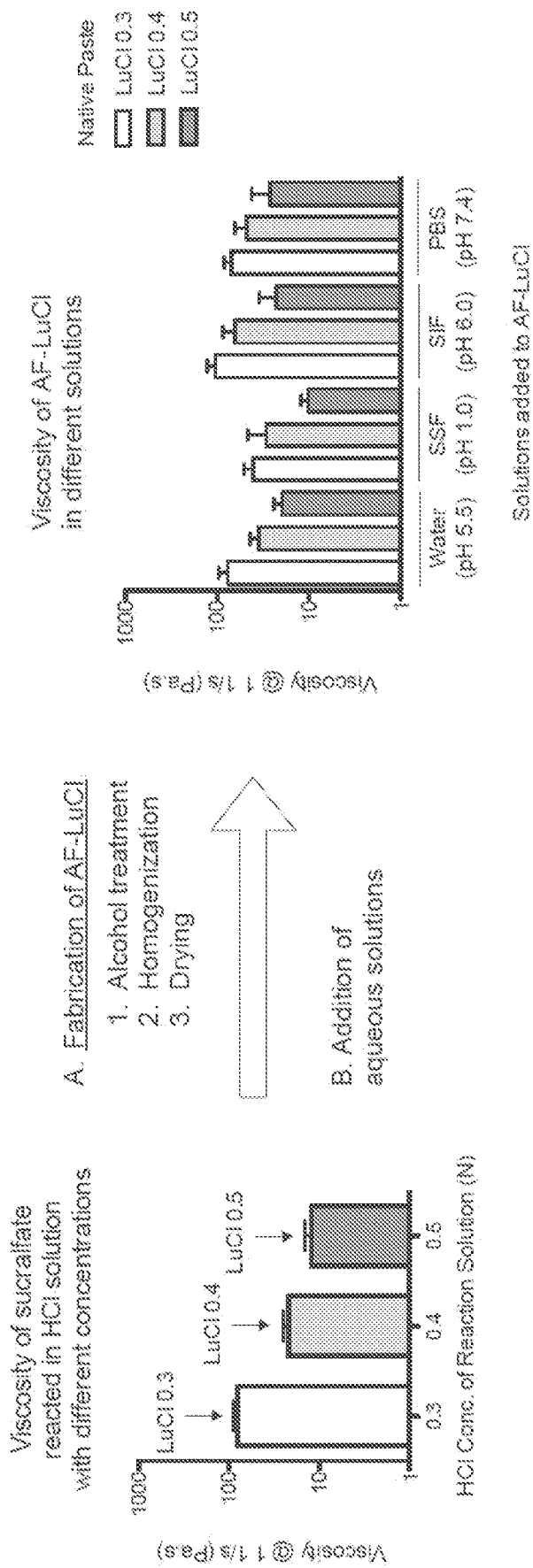
FIG. 9 is a pair of bar graphs showing the viscosity of acidified sucralfate paste (left graph) and hydrated AF-LuCI (right graph). Sucralfate pastes were fabricated from different concentration of HCl solution (0.3-0.5N) and were treated with ethanol to fabricate AF-LuCIs. The AF-LuCI particles could form the viscous sticky paste in all the pH that can be found in GI tract (i.e. pH 1-7).

In particular, FIG. 9 shows the viscosity of acidified sucralfate paste and hydrated AF-LuCI. The left graphs shows the results for sucralfate pastes fabricated from different concentration of HCl solution (0.3-0.5N) and were treated with ethanol to fabricate AF-LuCIs. The right graph shows the results of AF-LuCI particles that could form the viscous sticky paste in all the pH that can be found in GI tract (i.e. pH 1-7).

When the AF-LuCI particles were exposed to simulated gastric fluid (SGF, pH 1.0), simulated duodenal fluid (SDF, pH 3.5), simulated intestinal fluid (SIF, pH 6.5), and phosphate buffered saline (PBS, pH 7.4), they all generated similar viscous sticky pastes. For example, when the acidified sucralfate paste with the viscosity of 80 Pa·s was used to fabricate AF-LuCI, the resultant AF-LuCI particles could form pastes with the viscosity of 77 Pa·s, 41 Pa·s, 105 Pa·s, and 70 Pa·s in distilled water (pH 5.5), SGF, SIF, and PBS, respectively. The viscosity of the paste from AF-LuCI hydration was tunable using acidified sucralfate pastes with different viscosities. When the acidified sucralfate pastes with the viscosities of 80, 22, and 12 Pa·s were treated with alcohol to fabricate AF-LuCI, the resultant AF-LuCI particles could form the viscous pastes in distilled water with the viscosities of 77, 36, and 20 Pa·s.

Moreover, given that it is a rehydration process and the water content in the original paste that AF-LuCI was made from is about 5-20 w/w %, only minimal amount of water was required to generate the viscous sticky paste, whereas sucralfate requires at least 0.6-0.8 equivalents of acid for the reaction to generate the similar paste. This is clearly beneficial to form a coating instantly after contact with the wet luminal surface of gut.

Example 5—Film Thickness of Hydrated AF-LuCI Hydratable Compositions

Five hundred milligrams of AF-LuCI (excess) was added onto mucus-coated cellulose nitrate membrane (disk shape with 2 cm diameter) and DDW (pH 5.5), SGF (pH 1.0), or SIF (pH 6.5) was added immediately. After AF-LuCI becomes a paste and flow to form a layer (3-5 minutes), supernatant was removed and the paste-coated membrane was quickly frozen in −80° C. freezer to measure the thickness. The thickness of the mucus-coated cellulose nitrate membrane without AF-LuCI was separately measured as a baseline.

Figure 10:
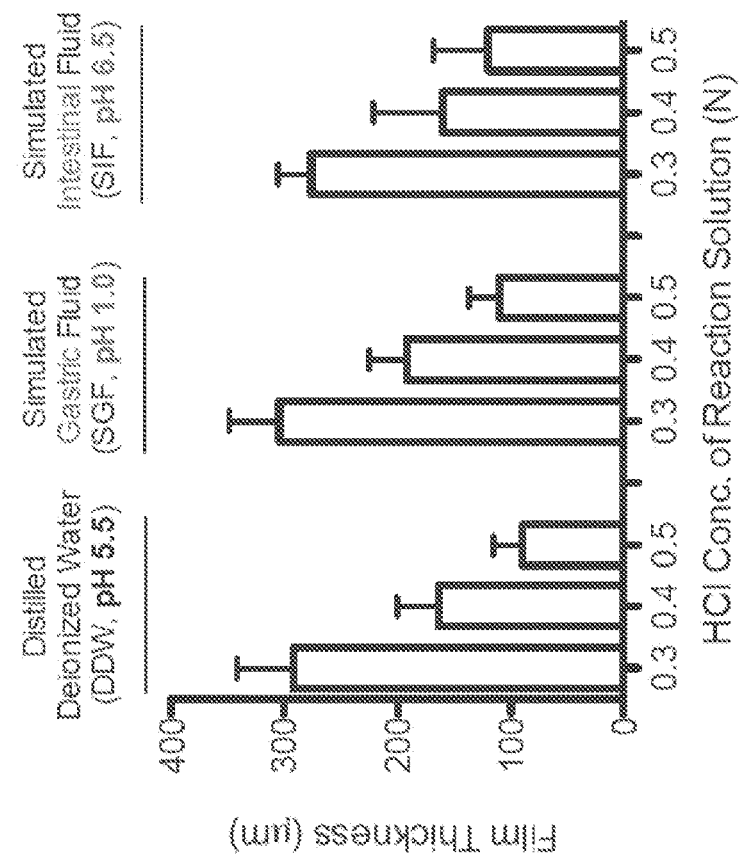
FIG. 10 is a bar graph showing the thickness of a layer formed by hydrated AF-LuCI paste. The AF-LuCI could form a layer of paste in contact with mucus surface in the GI tract including stomach (pH 1-3) and intestine (pH higher than 6).

The AF-LuCI could form a layer of paste in contact with mucus surface in GI tract including stomach (pH 1-3) and intestine (pH higher than 6). When AF-LuCI powders were added onto the mucus-coated cellulose nitrate membrane and added with distilled water (pH 5.5), SGF (pH 1.0), or SIF (pH 6.5), they could form a paste that slowly flowed over the mucus membrane to form a continuous layer with the thickness of 100-300 µm (FIG. 10). Sucralfate formed ~250 µm layer on the mucus-coated cellulose nitrate membrane only in SGF (pH 1.0) whereas it did not form any layer in distilled water or SIF.

Example 6—Stability of Hydrated AF-LuCI Hydratable Compositions

Five hundred milligrams of AF-LuCI (excess) was added onto mucus-coated cellulose nitrate membrane (disk shape with 2 cm diameter) and SIF (pH 6.5) was added immediately. After AF-LuCI became a paste and flow to form a layer (3-5 minutes), AF-LuCI coated membrane was placed on a 10 cm petri dish with 5 ml of SIF (pH 6.5). The petri dish was placed in a shaking incubator in 37° C. shaking in 500 rpm for 1 or 2 hours to apply shear as a test of stability over time. At the end of the selected time period, the AF-LuCI coated membrane was quickly frozen in −80° C. freezer to measure the thickness as a measure of stability. The thickness of the mucus-coated cellulose nitrate membrane without AF-LuCI was separately measured as a baseline.

Figure 11:
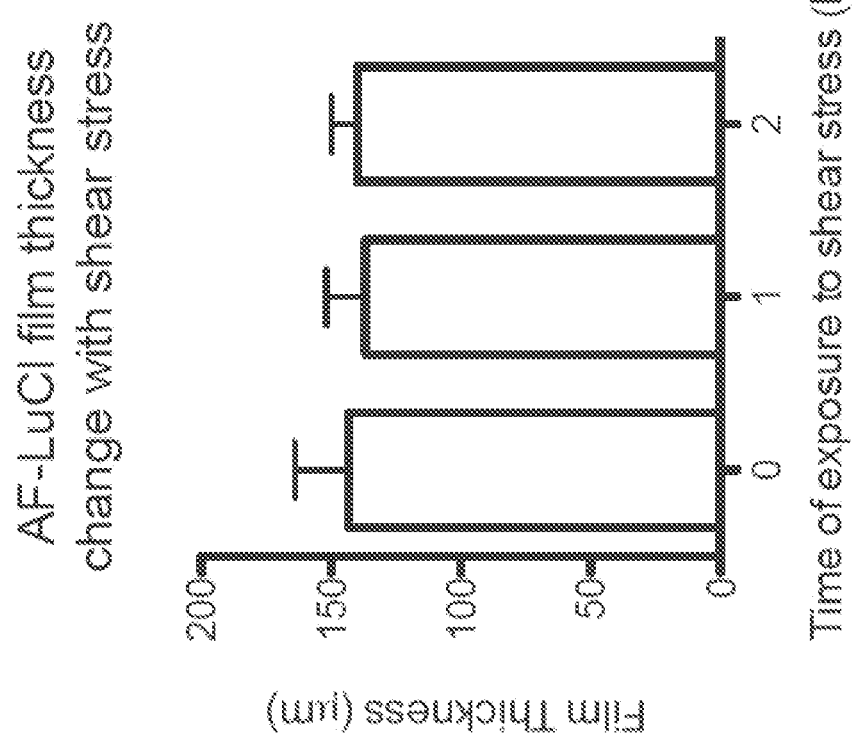
FIG. 11 is a bar graph showing the resistance to shear stress of the hydrated AF-LuCI pastes. The layer formed on mucus surface remains stable for at least 2 hours.

As shown in FIG. 11 the layer formed on mucus surface remains stable (no change in thickness) for at least 2 hours. These results indicate that the AF-LuCI particles can form a continuous layer on gut and the layer formed on the luminal mucus surface of gut should stay on the initial adhesion site during the duration of meal (i.e., 30-60 minutes and up to 2 hours) and have minimal change of the barrier properties during the meal.

Example 7—Swelling of Hydrated AF-LuCI Hydratable Composition Pastes

Five hundred milligrams of AF-LuCI 0.4 (excess) was added onto mucus-coated cellulose nitrate membrane (disk shape with 2 cm diameter) and SIF (pH 6.5) was added immediately. After AF-LuCI becomes a paste and flow to form a layer (3-5 minutes), AF-LuCI coated membrane was placed on a 10 cm petri dish with 10 ml of SGF (pH 1.0) or 10 ml of SIF (pH 6.5). The petri dish was placed in an incubator in 37° C. without shaking for 30, 60, and 120 minutes. The wet weights of resultant AF-LuCI coated membranes were measured to calculate swelling of AF-LuCI paste. The weight of the mucus-coated cellulose nitrate membrane without AF-LuCI was separately measured as a baseline.

Figure 12:
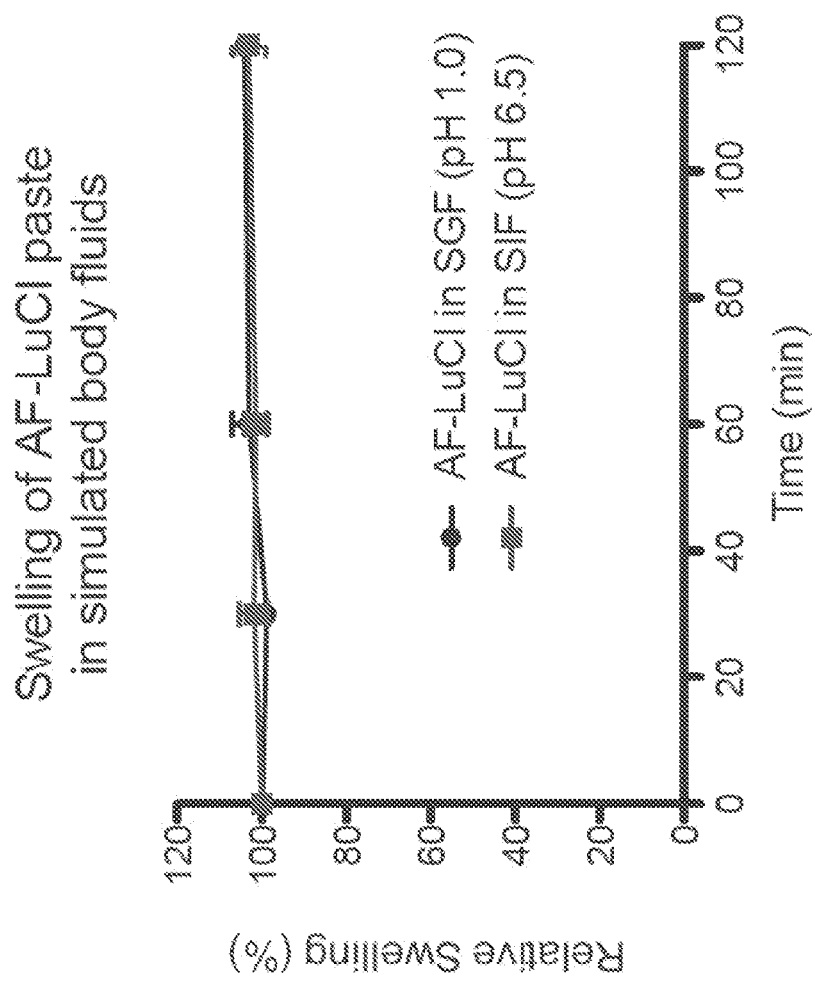
FIG. 12 is a graph showing the swelling of the hydrated AF-LuCI pastes. The hydrated AF-LuCI pastes showed significantly low swelling less than 5 w/w % for at least 2 hours in both SGF (pH 1.0) and simulated intestinal fluid (SIF)(pH 6.5).

As shown in FIG. 12, the layer formed on mucus surface showed significantly low swelling, less than 5 w/w %, for at least 2 hours in both SGF (pH 1.0) and SIF (pH 6.5). These results further indicate that the AF-LuCI particles can form a continuous layer on gut and the layer formed on the luminal mucus surface of gut should stay on the initial adhesion site during the duration of meal (i.e. 30-60 minutes) and have minimal change of the barrier properties during meal.

Example 8—Integrative Barrier Property Test Using Mucin-Coated Membranes

To examine the barrier properties of pastes formed from the new hydratable compositions in vitro, a mucin-coated membrane was prepared to mimic the mucus surface of the intestine. Specifically, a cellulose nitrate membrane (pore size: 0.2 Whatman, Germany) was incubated in a 3% w/v porcine stomach mucin (SigmaAldrich, USA) solution in PBS (pH 7.4) and gently shaken for 2 hours at room temperature. The membrane was washed with distilled deionized water (DDW, pH 5.5) to remove the excess mucin solution. The mucin-coated membranes were used within 1 hour following preparation.

To measure the thickness of the mucin layer, the mucin-coated membrane was lyophilized and imaged using scanning electron microscope (SEM) and the thickness of randomly selected positions was examined (average mucin layer thickness: ~100 μm). To test the nutrient barrier properties, 10 mg of sucralfate or AF-LuCI was added evenly to a mucin-coated membrane and vertically tilted for 1 minute. The material-attached to the mucin-coated membrane was mounted in the Franz-cell system and three milliliters of glucose solution (120 g/L) was added and samples were collected from the receiver part of the system after 5 minutes.

The permeation tests were performed in triplicate for each material. The glucose concentration was measured using high performance liquid chromatography (HPLC, Agilent, USA) with an analytical C18 column (Zorbax Eclipse XDB-C18, Agilent). The flow rate was 1 ml/min, the eluent was DDW, and the wavelength of UV detector was 195 nm. All results were normalized to a mucin-coated membrane without application of a test material (0% blocked).

Figure 13:
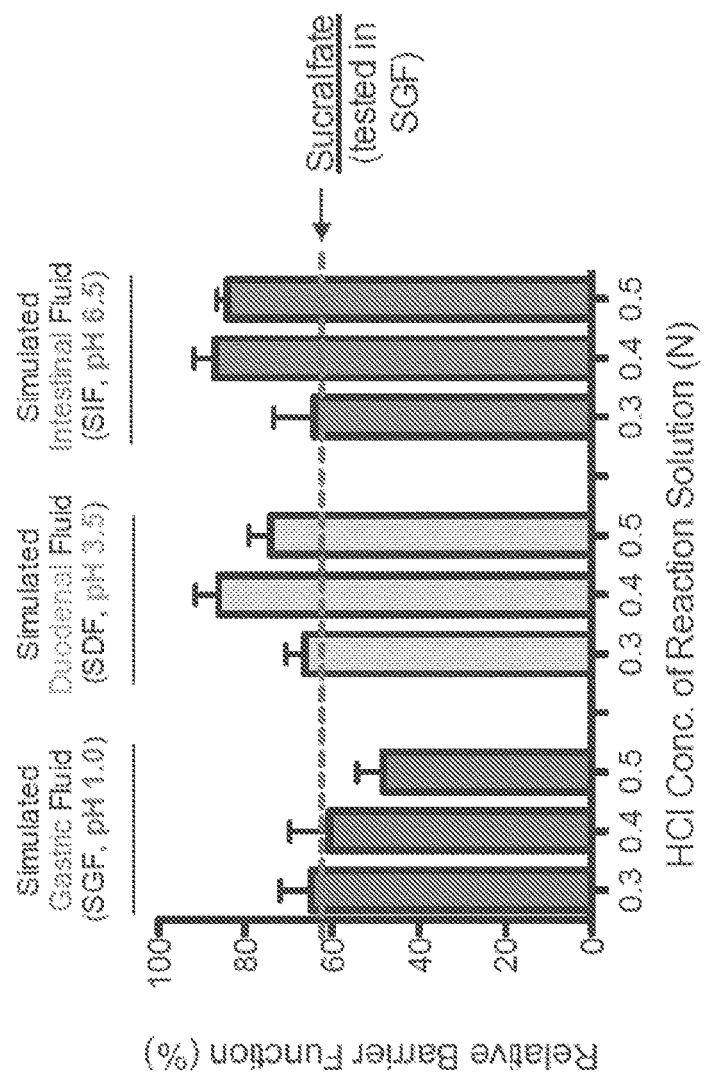
FIG. 13 is a series of bar graphs showing the barrier properties of AF-LuCI particles. The AF-LuCI particles showed excellent barrier properties on mucus substrate in SGF (pH 1.0), simulate duodenal fluid (SDF)(pH 3.5) and SIF (pH 6.5).

As shown in FIG. 13, the AF-LuCI particles showed excellent barrier properties on mucus substrate in SGF (pH 1.0), SDF (pH 3.5) and SIF (pH 6.5). In SGF, AF-LuCIs could block 40-70% of glucose penetration, and in higher pH environment using SDF and SGF, AF-LuCIs showed more enhanced barrier function (65-90% glucose blocked) that was higher than the barrier function of sucralfate in SGF (~60%). This enhanced barrier function is due to the formation of strong layer on the freshly harvested gut mucosa, and seems closely related to mucoadhesion of AF-LuCI.

Thus, when hydrated, the composition forms a barrier that when prepared at 10 mg/ml and applied to 1 cm$^2$ surface area cellulose nitrate filter with 0.45 micron holes in a Franz diffusion chamber exhibits less than 60% permeation of glucose 5 minutes after addition of 120 g/L glucose solution to the top chamber, and more preferably less than 40% permeation.

Example 9—In Vivo Evaluation of the Effect of AF-LuCI on Glucose Tolerance

Male Sprague Dawley (SD) rats between 330 and 350 grams were fasted overnight from 7 pm the night preceding the oral glucose tolerance test (15 hours). Two different formulations (hydrated paste and dry particles encapsulated in capsules) were tested. For the hydrated paste, 180 mg of AF-LuCI particles were hydrated using 0.9% normal saline before each gavage. The hydrated pastes were gavaged into stomach using gavage needles.

After oral gavages the animals were allowed access to water ad libitum. Rats gavaged with 0.9% normal saline were used as controls. Three hours after administration of capsules all animals underwent an oral glucose tolerance test (OGTT). In brief, all rats were gavaged with a glucose solution of 2 g/kg. Blood samples were collected prior to and 15, 30, 60, 90 and 120 minutes after administration of glucose solution. Blood was collected from the tail vein with a 30 gauge needle to measure blood glucose level using a glucometer (OneTouch UltraSmart®, LifeScan Inc., USA).

For the dry particle formulation, AF-LuCI particles were encapsulated in a hard gelatin capsule (Torpac®) to deliver compounds via oral gavage. Each capsule contained 30 mg of AF-LuCI particles. The 100% soluble capsules dissolve rapidly and completely in the stomach without enteric coating. Six capsules (total dose: 180 mg) were used without further coating and six capsules were manually covered with enteric coating ((15 w/v % Eudragit L100-55, 0.1 w/v % triethyl citrate (plasticizer), 0.5 w/v % talc (anti-tack) in 9.5 ml methanol and 0.5 ml water)) to ensure targeted delivery to the lower GI tract. Gavaging the capsules required an appropriate pill gavage needle and briefly anesthetizing the rats with isoflurane in oxygen. After oral gavages the animals were allowed to recover and access to water ad libitum. Rats gavaged with the same number of empty non-coated capsules were used as controls. Three hours after administration of capsules all animals underwent an OGTT as described above.

AF-LuCI particles were able to inhibit glucose response in SD rats with oral administration in both pre-hydrated formulation and dry formulation in capsules (FIGS. 14A-D). Rats gavaged with the hydrated formulation showed 18.7% reduction of glucose response (area under curve, AUC) and rats gavaged with the dry-capsules in non-coated capsules showed 19.2% reduction. Enteric-coated capsules that prevent release of AF-LuCI in the stomach and release particles in duodenum were also tested. With administration of enteric-coated capsules over three hours, rats showed 17.8% reduction in glucose response indicating the paste formed in duodenum can also block the nutrient sensing and absorption.

Figure 14B:
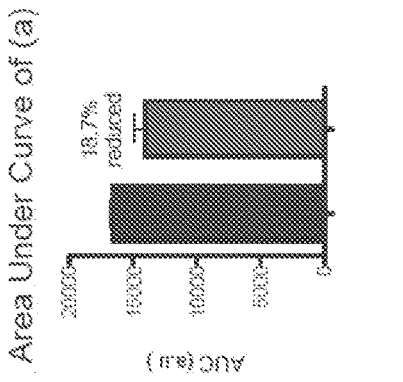
FIG. 14B is a bar graph showing the area under curve (AUC) of the OGTT curves in FIG. 14A.
Figure 14D:
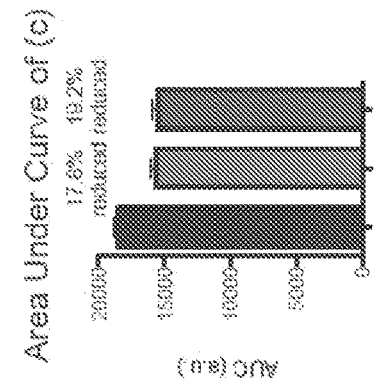
FIG. 14D is a bar graph showing the AUC of the OGTT curves in FIG. 14A.
Figure 14A:
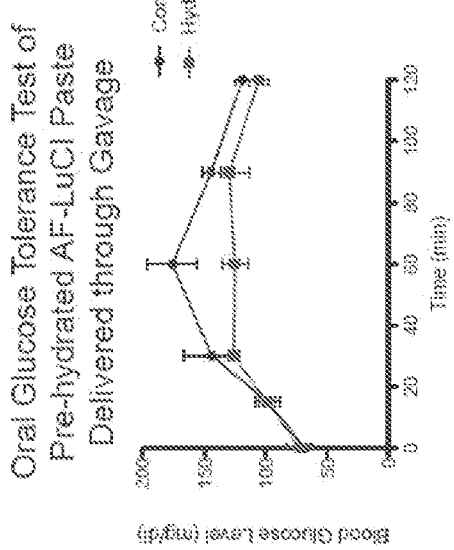
FIG. 14A is a graph showing the oral glucose tolerance test (OGTT) curves of rats gavaged with hydrated AF-LuCI (180 mg before hydration) and rats gavaged with the same amount of saline.
Figure 14C:
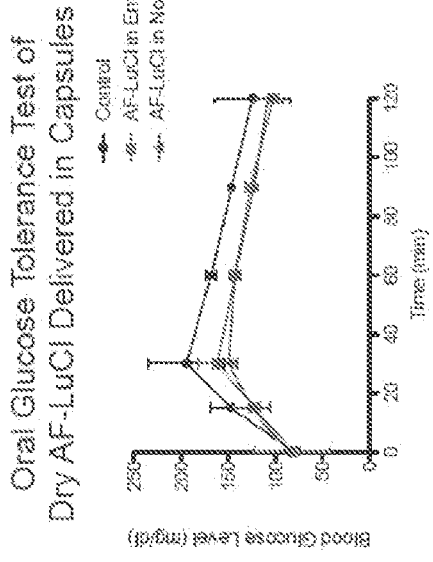
FIG. 14C is a graph showing the OGTT curves of rats gavaged with non-coated gelatin capsules containing 180 mg of dry AF-LuCI, rats gavaged with enteric-coated gelatin capsules containing 180 mg of dry AF-LuCI, and rats gavaged with empty non-coated gelatin capsules.

In particular, FIG. 14A shows the OGTT curves of rats gavaged with hydrated AF-LuCI (180 mg before hydration) and rats gavaged with the same amount of saline. FIG. 14B shows the area under curve (AUC) of the OGTT curves in FIG. 14A. FIG. 14C shows the OGTT curves of rats gavaged with non-coated gelatin capsules containing 180 mg of dry AF-LuCI, rats gavaged with enteric-coated gelatin capsules containing 180 mg of dry AF-LuCI, and rats gavaged with empty non-coated gelatin capsules. FIG. 14D shows the AUC of the OGTT curves in FIG. 14A. OGTT curves of rats gavaged with AF-LuCI in different formulations showed significant reduction of glucose response.

These in vivo results indicate that an oral administration of AF-LuCI in capsules can ensure successful decrease in glucose tolerance by possibly forming a mucoadhesive barrier in a targeted region of the GI tract (i.e. stomach and intestine).

Example 10—Polymerization of PAC in AF-LuCI

Experiments were performed to determine the degree of polymerization in AF-LuCI by using the titration-based methods as described in Nail, S. L., White, J. L. & Hem, S. L. Structure of Aluminum Hydroxide Gel I: Initial Precipitate. Journal of Pharmaceutical Sciences 65, 1188-1191 (1976); and Hem, J. D. & Roberson, C. E. Form and stability of aluminum hydroxide complexes in dilute solution. Geol Sury Water-Supply Pap(US)(United States) (1967). The degree of polymerization of PACs in AF-LuCI and sucralfate molecule was determined using titration method based on the reversible protonation of hydroxo linkages in the PAC backbone. Approximately 10 mg of AF-LuCI were treated with 0.1N, 0.2N, 0.3N, 0.4N and 0.5N HCl solutions in different tubes. The samples were vortexed for 5 seconds followed by 1-hour incubation. The supernatant of each sample was then collected and the pH was measured using a pH meter. The same procedures were performed with sucralfate. The pH of the HCl solutions was measured as the control group and the difference between the control and the treated groups was calculated. The difference in pH corresponds to the proton consumption and the amount of hydroxo linkages that were then used to calculate the number of aluminum per molecule.

Figure 15:
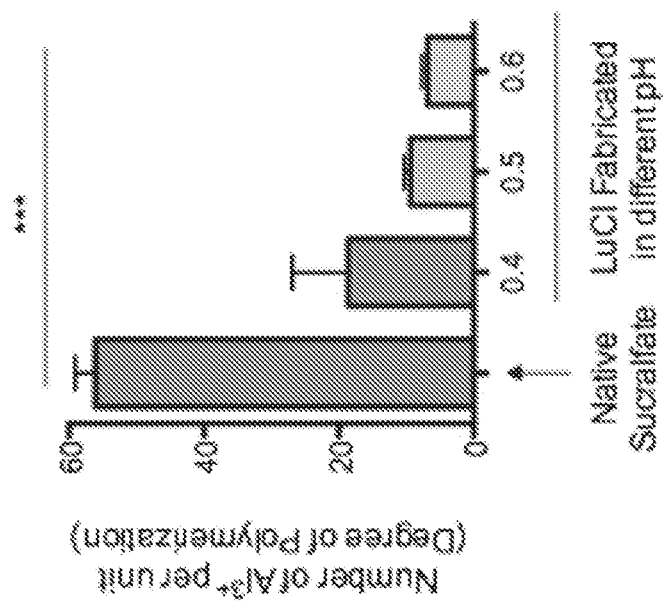
FIG. 15 is a graph showing degree of polymerization of PAC in sucralfate and AF-LuCI measured using titration method calculating the number of hydroxo linkages per aluminum.

The degree of polymerization of PAC in AF-LuCI (i.e. number of aluminum ions per PAC molecule) and the native sucralfate was analyzed. The numbers of aluminum ions per molecule of AF-LuCIs (18.6±8.4, 9.4±0.9, and 6.9±0.8 for AF-LuCIs fabricated using 0.4N, 0.5N, and 0.6N HCl solutions, respectively) were significantly lower than that of sucralfate (56.1±3.0 aluminum per molecule) (FIG. 15). FIG. 15 shows that PAC polymers in AF-LuCI are significantly shorter than in sucralfate indicating the polymers are less pH dependent and capable of forming liquid complex coacervate with anionic sucrose octasulfate (***<0.0001 in One-way ANOVA).

Example 11—Properties of Rehydrated Pastes

Figure 16:
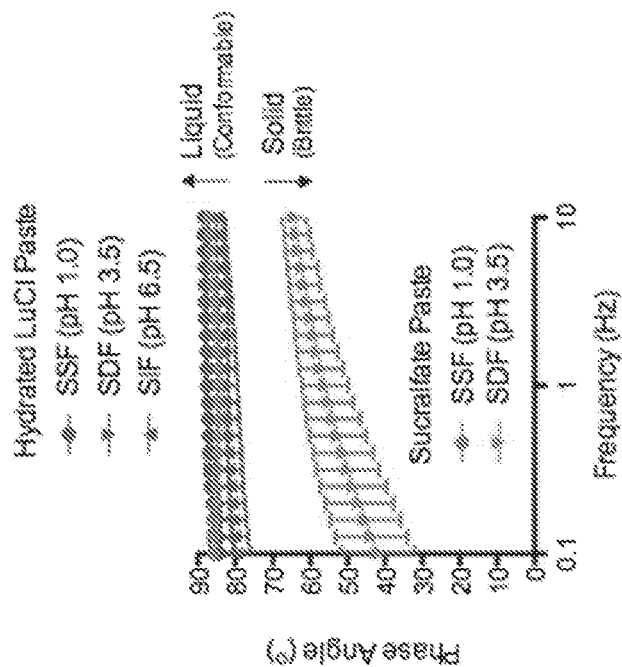
FIG. 16 is a graph showing change of rheological properties of dried AF-LuCI powder re-hydrated in different simulated gastrointestinal fluids.

Experiments were also performed to further determine the properties of rehydrated pastes. When the AF-LuCI paste hydrated in simulated gastric fluid (SGF, pH 1.0) was added with pH 3.5 SDF and pH 6.5 SIF, the phase angle of the resultant pastes were higher than 80° indicating that the resultant pastes are in liquid state that is conformable on a surface forming a continuous layer, while the sucralfate paste in pH 1.0 SGF added with SDF or SIF showed significant decrease of phase angle or formed weak brittle solid particles (FIG. 16). This shows that there was no significant change in the phase angle indicating that AF-LuCI forms liquid in pH-independent manner. The phase angle of acidified sucralfate paste drastically decreased in SDF (pH 3.5) forming weak solid aggregates. Thus, the AF-LuCI can be hydrated into a conformable viscous paste independent to the location in GI tract unlike the native sucralfate that formed particulate aggregates in stomach and didn't attach on duodenum and intestine. This pH-independent hydration behavior is due to the shorter PAC in AF-LuCI that is easier to solubilize in water and thus more accessible to form complex coacervate with the anions compared to the water-insoluble PAC of native sucralfate with higher degree of polymerization.

Figure 17:
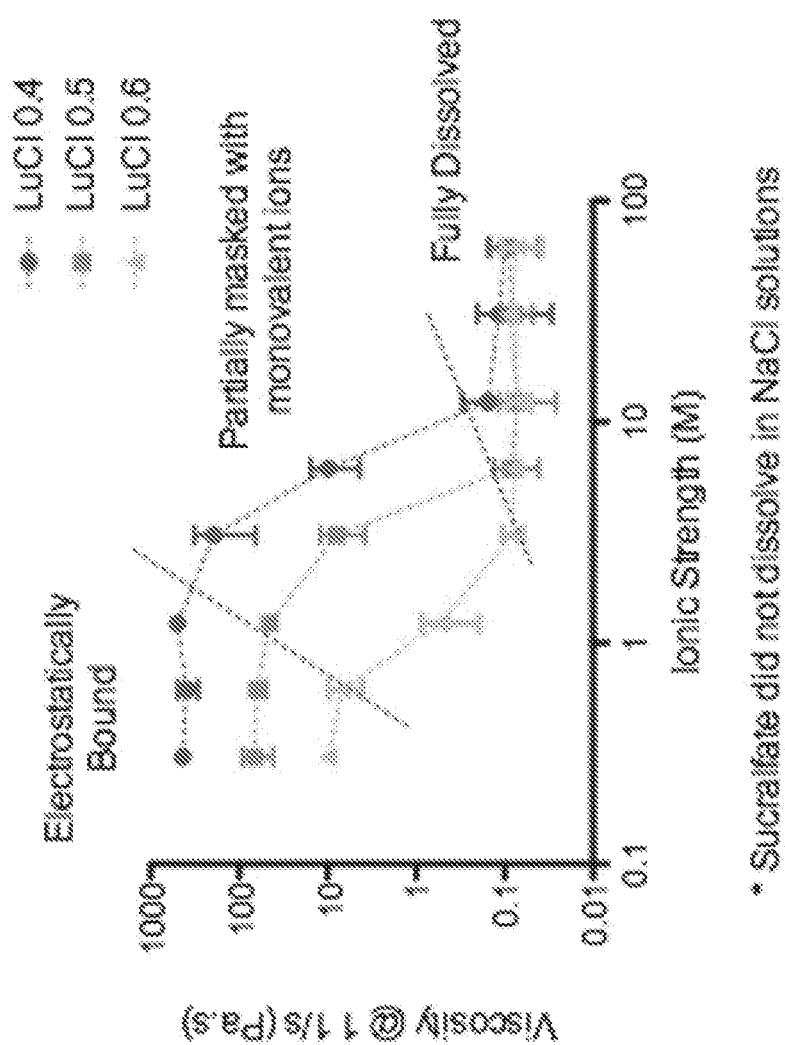
FIG. 17 is a graph showing change of viscosity of re-hydrated AF-LuCI in NaCl solutions with different ionic strength.

When AF-LuCI powders were added with NaCl solutions in different concentrations, they were gradually swollen with increasing NaCl concentrations to form a lower viscosity liquid due to partial masking of charged polymers with monovalent ions, and fully dissolved in higher concentration NaCl solutions above a certain critical level (FIG. 17). FIG. 17 shows that with increasing ionic strength, the viscosity of re-hydrated AF-LuCI pastes decreased due to partial masking of charged groups in PAC and sucrose octasulfate of AF-LuCI, and fully dissolved in NaCl solutions with ionic strength higher than a certain critical point. This is a characteristic behavior of complex coacervate system. This is a characteristic behavior of liquid complex coacervate system (See Wang, Q. & Schlenoff, J. B. The Polyelectrolyte Complex/Coacervate Continuum. Macromolecules 47, 3108-3116 (2014); de Kruif, C. G., Weinbreck, F. & de Vries, R. Complex coacervation of proteins and anionic polysaccharides. Current Opinion in Colloid & Interface Science 9, 340-349 (2004); Veis, A. & Aranyi, C. PHASE SEPARATION IN POLYELECTROLYTE SYSTEMS. I. COMPLEX COACERVATES OF GELATIN. J. Phys. Chem. 64, 1203-1210 (1960)). It indicates that the shorter and more hydrated PAC could form more flexible linkages with the anionic sucrose octasulfate forming the viscous liquid. AF-LuCI fabricated in higher concentration HCl required lower concentration NaCl solution to fully dissolve AF-LuCI (i.e. fully dissociate the PAC and sucrose octasulfate) suggesting that the shorter PAC has lower ionic binding energy contributing to its lower viscosity. Less than 5 w/w % of the native sucralfate was dissolved even in saturated NaCl solutions (~0.35 g/ml in water) and the remaining sucralfate remained suspended indicating that in the native sucralfate the two polyions are bound too strongly together and becomes liquid paste phase only with large amount of stomach acid that extensively breaks down the PAC.

Example 12—AF-LuCI Coating can Lower Glucose Response in Rats

Experiments were performed to assess how AF-LuCI forms a coating in vivo.

Figures 18A, 18B, 18C:
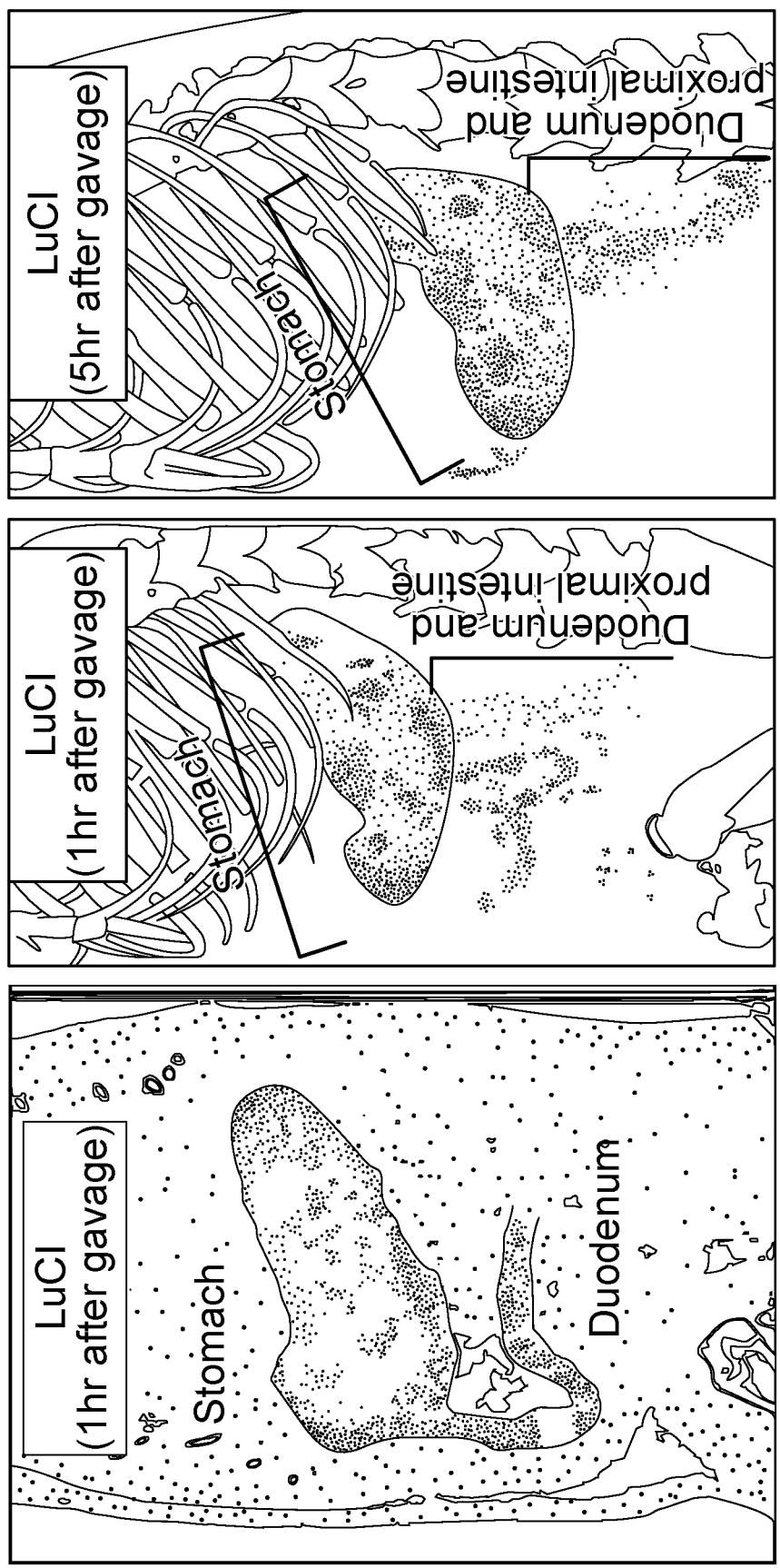
FIGS. 18A, 18B and 18C are images from micro-computed tomography (microCT) showing the behavior of AF-LuCI gavaged into rat stomach.

Sprague-Dawley (SD) rats were gavaged into the stomach with hydrated AF-LuCI pastes and imaged using micro-computed tomography (microCT). AF-LuCI pastes could be visualized on gastro-intestinal tissues without additional contrast agents owing to the presence of aluminum. For these experiments, rats were fasted overnight and gavaged directly into the stomach with 450 mg/kg rat of AF-LuCI paste hydrated in 0.9 w/v % normal saline solution. After 1 hr and 5 hr, the rats were anesthetized using isoflurane and imaged using microCT. The images showed that the AF-LuCI pastes formed a layer in the stomach and duodenum after 1 hr of the gavage and the layer was stable for the extent of the study (5 hr) (FIGS. 18A-18 C). FIG. 18A is a coronal plane view of SD rats gavaged with AF-LuCI 1 hr before the imaging. AF-LuCI formed a layer in stomach, duodenum and proximal intestine. FIGS. 18B and 18C are 3-dimensional views of SD rats gavaged with AF-LuCI (FIG. 18B) 1 hr and (FIG. 18C) 5 hr before the microCT imaging. AF-LuCI is attached on stomach, duodenum and proximal intestine at least for 5 hrs after gavage while sucralfate only formed sparsely scattered aggregates on the healthy mucosa When sucralfate was gavaged to SD rats, the microCT images only showed small aggregates on stomach and intestinal areas suggesting that the sucralfate did not form a layer. These data suggest that the AF-LuCI can form a coating on the luminal side of the GI tract with transient stability.

Experiments were then performed to assess if the AF-LuCI coating could lower glucose response. To evaluate the in vivo effect of the barrier coating from AF-LuCI on postprandial glucose response, SD rats were pre-gavaged with the AF-LuCI pastes and standard OGTT was performed. AF-LuCI at different dosage but also different viscosity. It was hypothesized that low viscosity product may lead to barrier formation in larger area and earlier duodenal coating (onset of action). For these studies, rats were fasted overnight and gavaged with AF-LuCI pastes (dose: 450-2,700 mg/kg rat; viscosity: high and low), or saline as a control. One or three hours later, glucose solution (2 g/kg rat) was gavaged and changes in serum glucose levels measured every 30 minutes over the subsequent 120 min (n=4 per arm). Tail vein blood was used to measure glucose levels using glucometer. The viscosity of the AF-LuCI paste had a significant impact on the reduction of blood glucose response (FIGS. 19A and 19B). The AF-LuCI formulation that forms a lower viscosity paste (viscosity: 5 Pa·s, 15% reduction with 450 mg/kg rat dose) showed significantly higher reduction of blood glucose responses compared to higher viscosity paste (viscosity: 36 Pa·s, 3% reduction with 450 mg/kg rat dose). The higher viscosity paste (36 Pa·s) exhibits a similar viscosity with the paste formed from native sucralfate by reacting with SGF. The time gap between AF-LuCI administration and glucose gavage also affects the reduction of blood glucose responses differently depending on the AF-LuCI formulations (FIG. 19C). 3 hr after treatment with 450 mg/kg rat lower viscosity AF-LuCI (i.e. 5 Pa·s), the reduction in glucose response decreased to 7%. In FIG. 19, AF-LuCI fabricated using 0.4N, 0.5N, and 0.6N HCl solution and rehydrated in 0.9 w/v % normal saline is denoted as "Viscosity High", "Viscosity Mid", and "Viscosity Low", respectively.

These results suggest that the oral administration of AF-LuCI can effectively lower the glucose response and the reduction in glucose responses can be maximized by altering physical properties of AF-LuCI (e.g., viscosity) that potentially modulates the coating properties (e.g., duration and location of coating).

In contrast, sucralfate selectively binds to ulcerated mucosa where the bicarbonate secretion is malfunctioned (i.e. acidic), while on bicarbonate-neutralized healthy mucosa sucralfate forms loosely bound discrete solid aggregates attached on the surface rather than forming a continuous layer. Computed tomography (CT) images and fluorescent microscopy images of the rats gavaged with sucralfate showed that sucralfate was sparsely scattered in the stomach and intestine in low density and washed out in a few hours. The neutralized pH on mucus surfaces also compromised the barrier function of sucralfate due to the change of rheological properties. When acidified sucralfate paste was added with solutions with pH higher than 1.0, the phase angle ($\delta$) in oscillatory rheological analysis gradually increased indicating the formation of weak solid aggregates. Furthermore, when sucralfate was applied on the mucus-coated membrane in pH 1.0 and added with solutions with higher pH (>2.0), the barrier function steeply decreased (16.5% glucose blocked in pH 4.0). As a result, when sucralfate was tested in oral glucose tolerance tests (OGTT) using normal Sprague-Dawley (SD) rats, the peak glucose values were similar at all other time points except for one time point at 5 min and there was no significant difference in the area under curve (AUC) between sucralfate and saline treated groups. These results suggest that AF-LuCI are more effective than sucralfate for lowering glucose response.

Example 13—AF-LuCI Coating Lowers Glucose Response Through Physical Barrier Effect Experiments were also performed to determine whether AF-LuCI coating has effect on glucose responses only through physical barrier effect and not through systemic effect. Rats were gavaged with AF-LuCI in the dose with the maximum effect (low viscosity, 450 mg/kg rat), and high dose glucose (2 g/g rat) was administered after an hour either through oral gavage (for OGTT) or through intraperitoneal injection (for IpGTT). In OGTT (FIG. 19D), the blood glucose responses were significantly reduced (FIG. 19E) and iAUC were reduced by 47.3% (FIG. 19F). In IpGTT (FIG. 19G), there was no difference in glucose responses in IpGTT curves (FIG. 19H), and in iAUC (FIG. 19I), suggesting that reduction of glucose response is through localized barrier coating but not through systemic effect.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A dehydrated acid-pretreated composition comprising particles comprising one or more aluminum cross-linked sulfated agents, wherein the composition has an aluminum content of less than 15.5% and can form a paste following contact with an aqueous liquid in the absence of acid, wherein the composition has the following chemical structure:

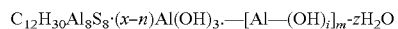

wherein x is less than or equal to 8;

$0 < n < x;$ m is greater than or equal to 2;

i=1, 2, or 3; and $z < 3(x-n) + (6-i)m.$

2. The composition of claim 1, wherein the composition comprises a complex coacervate comprising a complex of two or more oppositely charged agents where one agent is a sulfated agent.

3. The composition of claim 1, wherein the one or more sulfated agents are selected from the group consisting of sucralfate, sulfated dextran, sulfated dextrin, sulfated amylopectin, sulfated amylose, sulfated cellulose, carrageenan, chondroitin sulfate, glucose sulfate, sucrose sulfate, heparin, heparin sulfate, and raffinose sulfate.

4. The composition of claim 1, wherein the sulfated agent comprises sucralfate.

5. The composition of claim 1, further comprising a non-aqueous liquid carrier.

6. The composition of claim 5, wherein the composition has a viscosity in the range of 1 to 1000 Pa·s, regardless of the pH of the liquid.

7. The composition of claim 1, wherein the composition comprises particles ranging in size from about 0.1 to about 500 microns.

8. The composition of claim 1, wherein when hydrated, the composition forms a barrier that when prepared at a concentration of 10 mg/ml and applied to a 1 cm² surface area cellulose nitrate filter with 0.45 micron holes in a Franz diffusion chamber device exhibits less than 60% permeation of glucose 5 minutes after addition of a 120 g/L glucose solution to a top chamber of the Franz diffusion chamber device.

9. The composition of claim 1, wherein the composition releases less than about 2.0 weight/weight percent of its original aluminum content in the presence of an aqueous liquid.

10. The composition of claim 1, wherein the composition releases less than 0.5% aluminum by weight in the presence of an aqueous liquid and when administered to a subject forms an effective nutrient barrier in the gastrointestinal tract.

11. The composition of claim 1, wherein the particles are further cross-linked to an antimicrobial agent.

12. The composition of claim 1, wherein the composition comprises a biologically active substance.

13. The composition of claim 12, wherein the biologically active substance comprises any one or more of enzymes, receptors, neurotransmitters, hormones, cytokines, cell response modifiers, antibodies, vaccines, haptens, toxins, interferons, ribozymes, anti-sense agents, plasmids, DNA, and RNA.

14. The composition of claim 1, wherein the average number of aluminum ions per molecule in the composition is less than 40.

15. A method of modulating nutritional absorption in a subject having a disorder in need of such treatment, the method comprising
   selecting a subject suffering from a disorder requiring modulation of nutritional absorption; and
   administering to the subject a therapeutically effective amount of a composition of claim 1.

16. The method of claim 15, wherein the disorder is type II diabetes or obesity.

* * * * *

UNITED STATES PATENT AND TRADEMARK OFFICE
CERTIFICATE OF CORRECTION

| | |
|---|---|
| PATENT NO. | : 10,973,846 B2 |
| APPLICATION NO. | : 15/763018 |
| DATED | : April 13, 2021 |
| INVENTOR(S) | : Jeffrey M. Karp et al. |

It is certified that error appears in the above-identified patent and that said Letters Patent is hereby corrected as shown below:

In the Specification

In Column 1, Line 13, insert -- STATEMENT OF FEDERALLY SPONSORED RESEARCH
This invention was made with government support under Grant Nos. DK084064, and RR025757 awarded by the National Institutes of Health. The government has certain rights in the invention. --

Signed and Sealed this
Twenty-third Day of May, 2023

Katherine Kelly Vidal
*Director of the United States Patent and Trademark Office*